(12) United States Patent
Haro Villar et al.

(10) Patent No.: US 9,012,405 B2
(45) Date of Patent: Apr. 21, 2015

(54) CITRULLINATED FIBRIN-FILAGGRIN CHIMERIC POLYPEPTIDE CAPABLE OF DETECTING THE ANTIBODIES GENERATED IN RHEUMATOID ARTHRITIS

(75) Inventors: Isabel Haro Villar, Madrid (ES); José M. Gomora Elena, Madrid (ES); Luisa M Perez Rodríguez, Madrid (ES); Raimon Sanmarti Sala, Barcelona (ES)

(73) Assignees: Consejo Superior de Investigaciones Cientificas (ES); Fundacio Clinic per a la Recerca Biomedica (ES)

( * ) Notice: Subject to any disclaimer, the term of this patent is extended or adjusted under 35 U.S.C. 154(b) by 1154 days.

(21) Appl. No.: 12/598,284

(22) PCT Filed: Apr. 30, 2008

(86) PCT No.: PCT/ES2008/070087
§ 371 (c)(1),
(2), (4) Date: Apr. 26, 2010

(87) PCT Pub. No.: WO2008/132264
PCT Pub. Date: Nov. 6, 2008

(65) Prior Publication Data
US 2010/0216173 A1 Aug. 26, 2010

(30) Foreign Application Priority Data
Apr. 30, 2007 (ES) .................. 200701167

(51) Int. Cl.
| | |
|---|---|
| *G01N 33/53* | (2006.01) |
| *C07K 7/64* | (2006.01) |
| *G01N 33/566* | (2006.01) |
| *G01N 33/564* | (2006.01) |
| *C07K 14/75* | (2006.01) |
| *C07K 14/78* | (2006.01) |
| *G01N 33/68* | (2006.01) |
| *A61K 38/00* | (2006.01) |

(52) U.S. Cl.
CPC .............. *G01N 33/564* (2013.01); *A61K 38/00* (2013.01); *C07K 14/75* (2013.01); *C07K 14/78* (2013.01); *C07K 2319/40* (2013.01); *G01N 33/686* (2013.01); *G01N 2800/102* (2013.01)

(58) Field of Classification Search
None
See application file for complete search history.

(56) References Cited

U.S. PATENT DOCUMENTS 7,022,485 B1 4/2006 Serre

FOREIGN PATENT DOCUMENTS

WO WO 98/22503 5/1998
WO WO 03/050542 A2 6/2003

OTHER PUBLICATIONS

Perez, M.L. et al. "Synthesis of overlapping fibrin citrullinated peptides and their use for diagnosing rheumatoid arthritis".Chem. Biol. Drug Des Jan. 10, 2006. vol. 68, No. 4 pp. 194-200.*
Guo et al. "Protein tolerance to random amino acid change". PNAS vol. 101 No. 25 9205-9210 Jun. 22, 2004.*
Lesk et al. "Prediction of Protein Function from Protein Sequence and Structure", p. 27 and 28, downloaded Nov. 13, 2012.*
Perez et al. "Antibodies to Citrullinated Human Fibrinogen Synthetic Peptides in Diagnosing Rheumatoid Arthritis" J. Med. Chem. 2007, 50, 3573-3584.*
International Search Report of PCT/ES2008/070087 mailed Sep. 4, 2008.
Arnelt F.C., American College of Rheumatology (ACR), Arthritis and Rheumatism,1988, 31:315-24.
Gomara, M.J., Journal of Immunological Methods, 2000, 234 (1-2), 23-34.
Nijenhuis S., Clinica Chimica Acta, 2004, vol. 350, Nos. 1-2, pp. 17-34.
Perez T., Letters in Peptide Science, 2002, 9, 291-300.
Perez T., Journal of Peptide Science, 2006, 12: 267-278.
Perez M.L., Chem. Biol. Drug Des., 2006, vol. 68, No. 4, pp. 194-200.
Perez M.L., J. Med. Chem., 2007, vol. 50, No. 15, pp. 3573-3584.
Pruijn, Arthritis Research & Therapy, 2010, 12:203, 1-8.
Sanmartí, Arthritis Research & Therapy, 2009, 11:R135. p. 1-9, http://arthritis-research.com/content/11/5/R135.
Saraux A., Arthritis & Rheumatism, 2001, 44:11, 2485-2491.
Sebbag, Eur. J. Clin. Immunol., 2006, 36: 2250-2263.
Van Gaalen F.A., Ann. Rheum. Dis., 2005, vol. 64, No. 10, 1510-1512.
Vossenaar, E.R., Bioessays, 2003, 25: 1106-1118.
Schellekens et al. "The Diagnostic properties of rheumatoid arthritis antibodies recognizing a cyclic citrullinated peptide."*Arthritis & Rheumatism.* vol. 43. No. 1. Jan. 2000. pp. 155-163.
Schellekens et al. "Citrulline is an Essential constituent of Antigenic Determinants recognized by Rheumatoid Arthritis-specific Autoantibodies." *J. Clin. Invest.* vol. 101. No. 1. Jan. 1998. pp. 273-281.
French et al., "What is a Conservative Substitution?", Journal of Molecular Evolution, 1983, vol. 19, pp. 171-175.

* cited by examiner

*Primary Examiner* — Robert A Wax
*Assistant Examiner* — Danah Al-Awadi
(74) *Attorney, Agent, or Firm* — Merchant & Gould P.C.

(57) ABSTRACT

The present invention concerns a chimeric polypeptide, capable of detecting the antibodies generated in rheumatoid arthritis, comprising at least two citrullinated peptide sub-units: (i) one derived from the α or β chain of the fibrin and (ii) a second derived from the filaggrin. In addition, the invention comprises an antigenic composition, a method and a kit for the diagnosis of rheumatoid arthritis, from the detection of the autoantibodies generated during the course of said disease.

10 Claims, 13 Drawing Sheets

FIG. 4
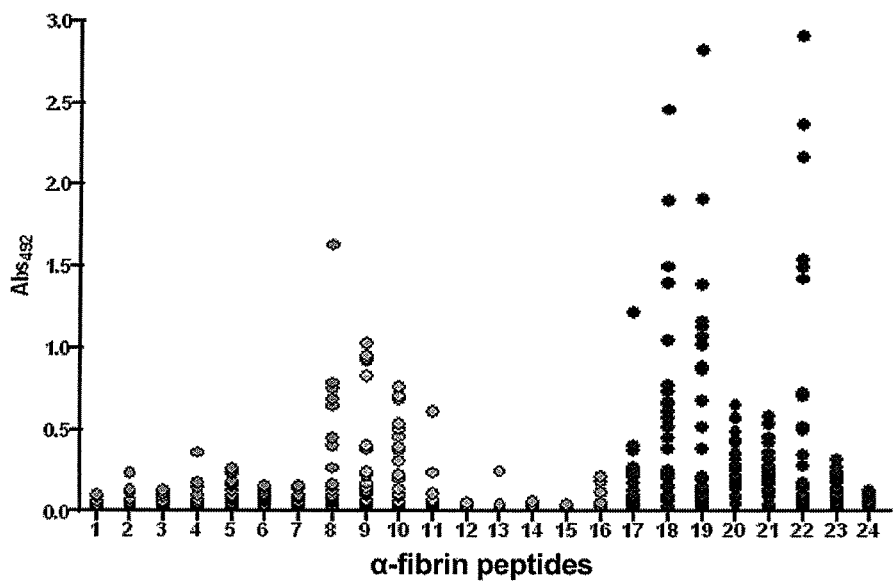
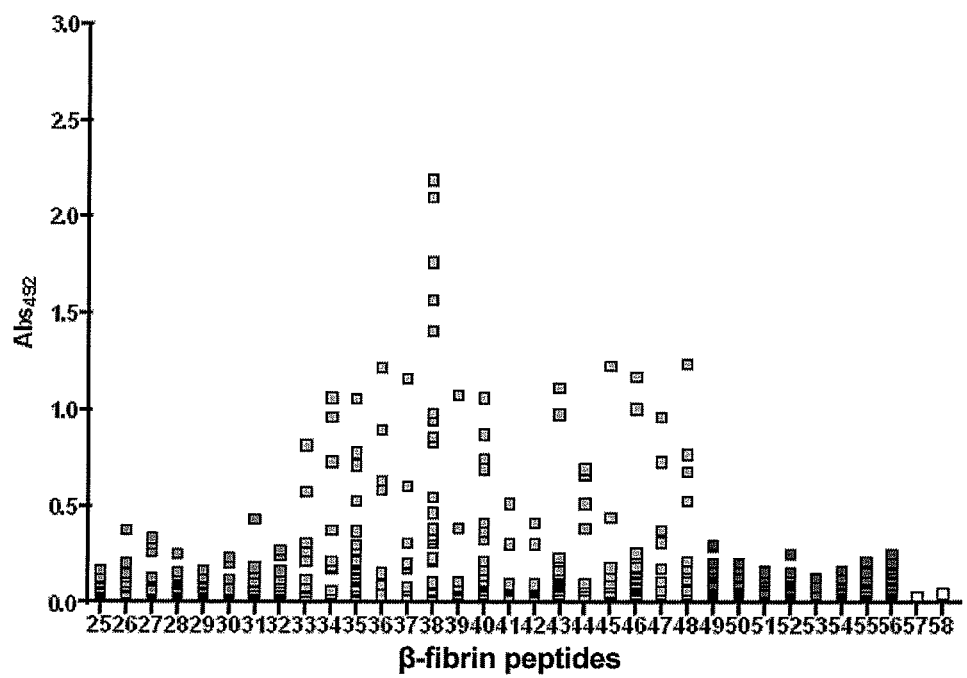

FIG. 6
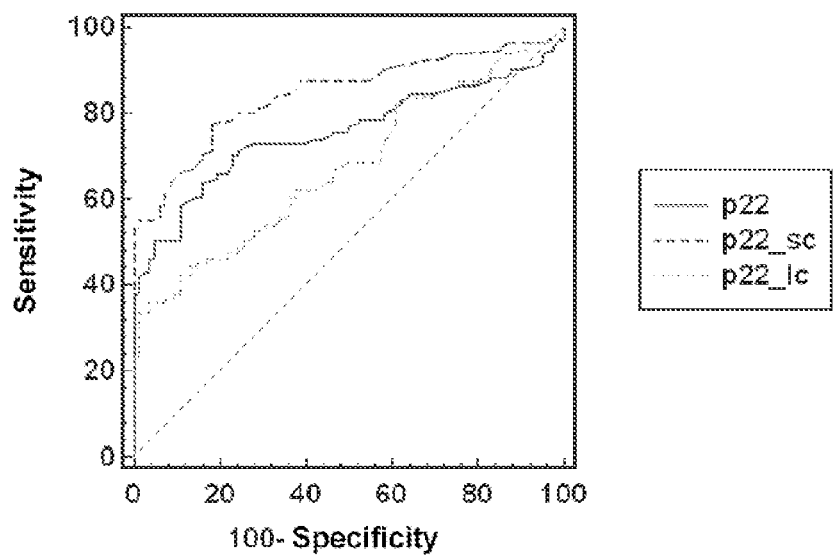
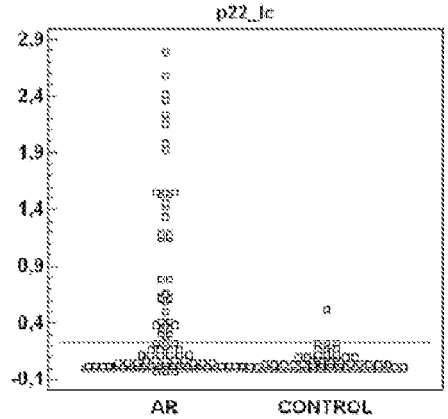

FIG. 7
A
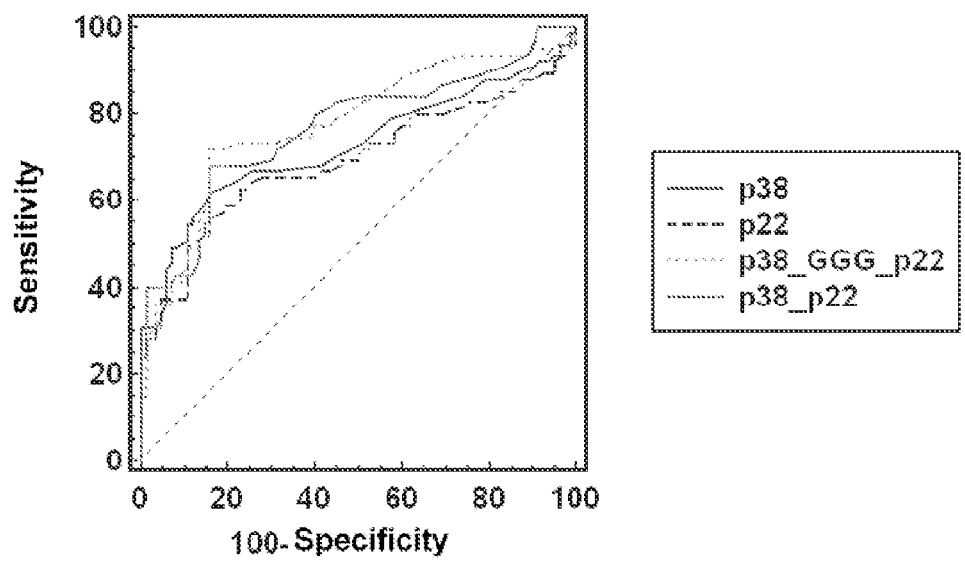
B
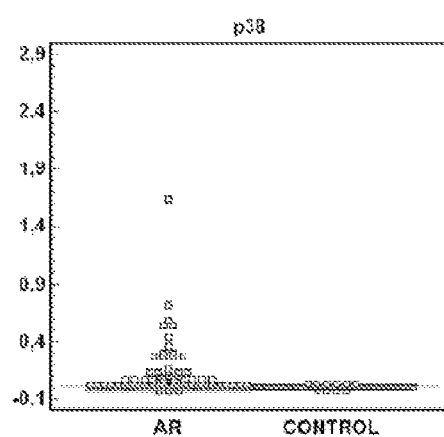
C
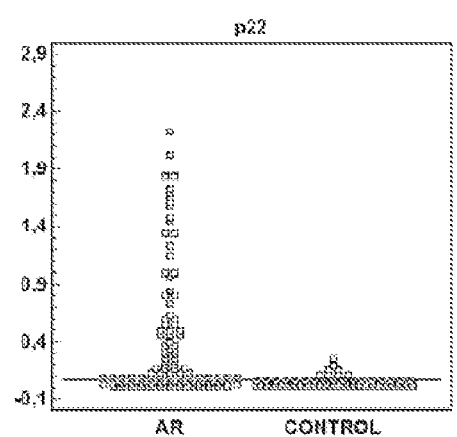
D
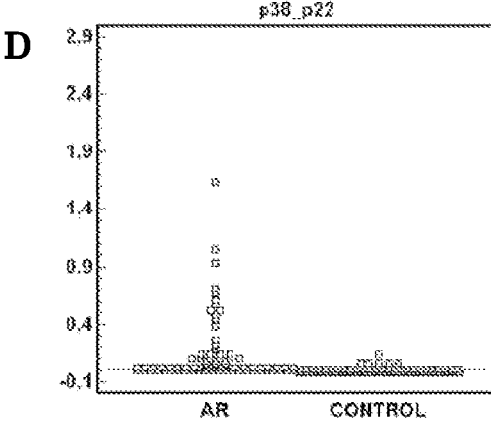
E
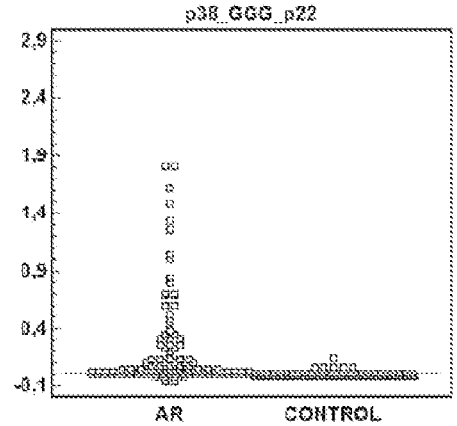

FIG. 8
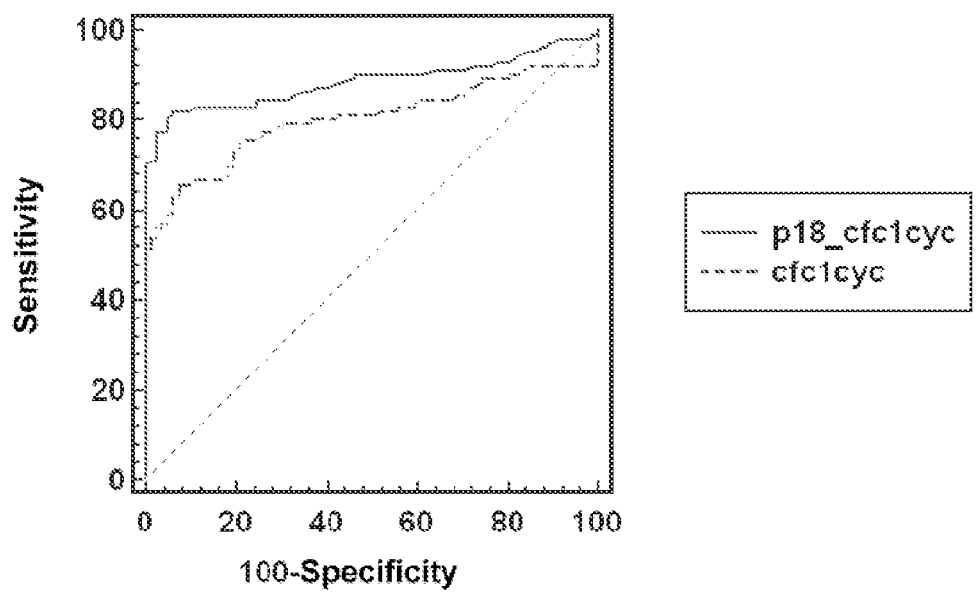
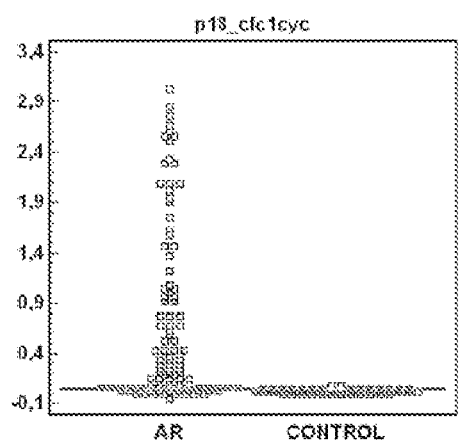 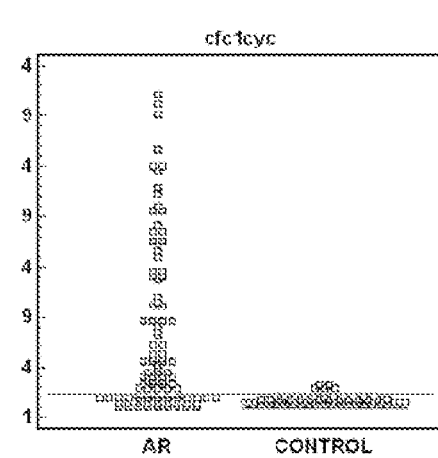

CITRULLINATED FIBRIN-FILAGGRIN CHIMERIC POLYPEPTIDE CAPABLE OF DETECTING THE ANTIBODIES GENERATED IN RHEUMATOID ARTHRITIS

This application is a National Stage Application of PCT/ES2008/070087, filed 30 Apr. 2008, which claims benefit of Serial No. P200701167, filed 30 Apr. 2007 in Spain and which application(s) are incorporated herein by reference. To the extent appropriate, a claim of priority is made to each of the above disclosed applications.

FIELD OF THE INVENTION

The present invention relates to a chimeric polypeptide, capable of detecting the antibodies generated in rheumatoid arthritis, which comprises at least two citrullinated peptide subunits: (i) one from the α or β chain of fibrin and (ii) a second from filaggrin. Furthermore, the invention comprises an antigenic composition, a method and a kit for the diagnosis and prognosis of rheumatoid arthritis, from the detection of the autoantibodies generated during the course of said disease.

PRIOR ART

Rheumatoid arthritis (RA) is one of the most common autoimmune diseases, with an unknown origin and which affects 0.5-1% of the population, progressively destroying the joints, causing deformity and loss of function in them, in addition to producing systemic complications.

In this disease the intensive therapy applied in initial stages offers very positive results, its early diagnosis being fundamental. The classification for RA according to the American College of Rheumatology (ACR) (Arnelt F C, et al. *Arthritis Rheum*. 1988; 31:315-24) is based on purely clinical parameters, although these criteria are not useful for the early diagnosis of RA (Saraux A, et al. *Arthritis Rheum* 2001; 44: 2485-91).

At present, there are different serological methods which permit the diagnosis of RA and they distinguish them from other similar pathologies in early phases of their evolution. In this sense, a series of specific antibodies for RA is known, such as: antiperinuclear factor (APF), antifilaggrin antibodies (AFA) and antikeratin antibodies (AKA). The epitopes recognized for these antibodies (citrullinated anti-protein autoantibodies) are generated by post-translational modifications which consist of the deimination of arginine to citrulline by the enzyme peptidyl arginine deiminase (Vossenaar E R, et al. *Bioessays* 2003; 25: 1106-18).

One of the most specific tools in diagnosing RA consists of the detection of the autoantibodies generated against peptides or citrullinated proteins, them constituting one of the most effective serological markers of this pathology that are known (Nijenhuis S, et al. *Clin. Clin. Acta* 2004; 350: 17-34). Even, the most effective and commercially most widely available kits (ELISA) for the diagnosis of RA are based on citrullinated peptides (CCP-1 and CCP-2) derived specifically from the filaggrin protein (Nijenhuis S, et al. 2004).

Other proteins of the synovial tissue that can be citrullinated are the α and β chains of fibrin and the Sa antigen or citrullinated vimentin. Recently, Sebbag et al (Sebbag et al *Eur. J. Clin. Immunol.* 2006, 36: 2250-2263) identified 18 peptides derived from fibrin protein, two of which, called [Cit$^{60,72,74}$] β-fibrin (60-74) and [Cit$^{38,42}$] α-fibrin (36-50) and localized in the globular domain of the protein, were capable of reacting to all the positive serums for citrullinated anti-protein autoantibodies. These results have been corroborated by recent studies (Pérez, et al *Chem. Biol. Drug Des.* 2006, 68, 194-200; U.S. Pat. No. 7,022,485), where the reactivity of the peptides derived from fibrin in the diagnosis of RA have been analysed, thus confirming their use for the development and improvement of the efficacy of the current diagnosis systems.

EXPLANATION OF THE INVENTION

There is a growing interest in developing specific tests which improve the diagnosis of RA as well as their early differentiation with respect to other rheumatic diseases which affect the joints and connective tissue, especially in patients with a poor prognosis or those with an earlier development of the disease. The incorporation of these tests in clinical practice makes it possible to identify those patients who require more intensive therapies from the very time of diagnosis of the disease, thus allowing a greater control thereof and, consequently avoiding as far as possible joint destruction and improving the prognosis of the disease.

The authors of the present invention, in their desire to improve the RA diagnosis systems currently used, have surprisingly discovered a series of citrullinated peptides of the α and β chains of fibrin with special sensitivity and specificity to the citrullinated anti-protein autoantibodies, hereinafter autoantibodies, which are generated during the development of RA. Furthermore, one of these citrullinated peptides of the α chain of fibrin was covalently bound to a cyclic peptide of filaggrin obtaining a chimeric polypeptide (fibrin-filaggrin) which was capable of complementing or improving the results of sensitivity and specificity obtained with peptides CCP-1 and CCP-2 (Immunoscan RA).

Thus, a first aspect of the invention relates to a chimeric polypeptide, which comprises at least two citrullinated peptide subunits and covalently bonded, capable of interacting with autoimmune antibodies generated during RA, where:

a. a subunit (a) comprises at least 85% homology, preferably at least 90%, more preferably at least 93%, even more preferably at least 95% and still more preferably at least 98%, with a fragment of at least 7 amino acids of any of the α and β chains of fibrin, preferably with a length between 10 and 18 amino acids, and b. a second cycled subunit (b) which comprises at least 85%, preferably at least 90%, more preferably at least 93%, even more preferably at least 95% and still more preferably at least 98%, homology with a fragment of at least 7 amino acids of filaggrin protein, preferably with a length between 10 and 18 amino acids.

In a preferred embodiment of this aspect of the invention the subunit b comprises at least two cysteine amino acids between which is formed a disulfide bridge to cycle said subunit. Preferably, these cysteines come from a serine-cysteine substitution.

In a more preferred embodiment of this aspect of the invention the filaggrin fragment from which subunit b is obtained is that comprised between positions 306 and 324 of said protein, and in an even more preferred embodiment the sequence between positions 306 and 324 of the filaggrin is SEQ ID NO:7.

In an even more preferred embodiment subunit (b) comprises the sequence SEQ ID NO:1 (cfc1cyc).

In a more preferred embodiment of this aspect of the invention the fibrin fragment from which subunit a is obtained is the fragment which goes from position 617 to 631 of α-fibrin, or that between positions 43 and 62 of β-fibrin. In a preferred embodiment the sequence between positions 617 and 631 of the α-fibrin is SEQ ID NO:8. In an even more preferred embodiment the sequence between positions 43-62 of the β-fibrin is SEQ ID NO:9.

In a still even more preferred embodiment of this aspect of the invention the subunit (a) of the chimeric polypeptide comprises the sequence selected from the group:
  a. SEQ ID NO:2 (p18),
  b. SEQ ID NO:3 (p19), or
  c. SEQ ID NO:4 (p22), In an even more preferred embodiment of this aspect of the invention the subunit (a) of the chimeric polypeptide comprises the sequence SEQ ID NO:5 (p38).

In another preferred embodiment of the invention the chimeric polypeptide comprises SEQ ID NO:6 (p18-cfc1cyc).

In an also preferred embodiment of the invention the chimeric polypeptide, according to any of the previous aspects of the invention it is marked or conjugated with transporting molecules.

Hereinafter, these citrullinated chimeric polypeptides will be known as "chimeric polypeptide of the invention". Said polypeptides can be obtained by procedures very well known in the state of the art, such as the chemical synthesis of peptides in solid phase (see material and methods).

A second aspect of the invention relates to citrullinated peptides of the α and β chains of fibrin where said peptides have any of the sequences selected from the group: p18, p19, p22 and p38 or analogous sequences (analogous peptides), where said citrullinated peptides and analogous peptides are capable of interacting with the specific autoantibodies of RA. In a preferred embodiment of the invention the peptides are cycled and in an embodiment the cycling is carried out from two cysteines, preferably from a serine-cysteine substitution. Hereinafter, these citrullinated peptides shall be known as "peptides of the invention."

A third aspect of the invention relates to an antigenic composition for the diagnostic and/or prognostic analysis of RA which comprises at least one of the peptides of the invention, the chimeric polypeptide of the invention or combinations thereof. Hereinafter, this composition shall be known as "antigenic composition of the invention".

A fourth aspect of the invention relates to a method for the detection of specific autoantibodies of RA in a biological sample which comprises:
  a. Placing in contact a biological sample with at least one of the following compounds: a peptide of the invention, a chimeric polypeptide of the invention, an antigenic composition of the invention.
  b. Detecting the interaction between the specific autoantibodies and the peptides of the invention, the chimeric polypeptide or antigenic composition of step (a), by any useful methodology, which can be any of the numerous and very well known methods in the state of the art (for example, through peptide marking, or the mediation of optical density of the sample, etc.) or any other method.

In a preferred embodiment of this aspect of the invention, more than one chimeric polypeptide of the invention is placed in contact with the biological sample. In another embodiment of the invention, the biological sample is placed in contact with one or more of the chimeric polypeptides of the invention and the polypeptide CCP-2.

A fifth aspect of the invention relates to a kit for the diagnosis and prognosis of RA which comprises at least one of the peptides of the invention, the chimeric polypeptide of the invention or the antigenic composition of the invention (antigens), preferably said kit shall comprise the reagents and buffers necessary to allow the formation of the antibody-antigen complex.

DEFINITIONS

The term "derived peptide or polypeptide" refers throughout the description to peptides obtained from regions or fragments of at least 7 amino acids of the filaggrin protein or of the α and β chains of fibrin. These derived peptides may have suffered modifications (e.g.: cyclings, deiminations, etc), which have reduced their homology with the initial sequence of the protein from which they derive. One example of these peptides are the groups of peptides known as CCP-1 and CCP-2.

The term "CCP-1 peptides" refers throughout the description to cyclic peptides derived from filaggrin.

The term "CCP-2 peptides" refers throughout the description to peptides with a degree of sensitivity and specificity for the detection of RA greater than that reached with the CCP-1 peptides. Throughout the assays, which are shown in the description, the peptides of the invention are compared with the CCP-2 peptides obtained from the commercial Immunoscan kit (Immunoscan RA; Eurodiagnostica, distributed by Diasorin, Madrid, Spain).

The term "analogous peptides of polypeptides" refers to peptides where at least one of their amino acids has been substituted by another one of similar characteristics as indicated below:
  Polar neutral, hydrophilous or (polar): serine (Ser), threonine (Thr), cysteine (Cys), asparagine (Asn) and glutamine (Gln).
  Non-polar neutrals, apolar or hydrophobic: glycine (Gly), alanine (Ala), valine (Val), leucine (Leu), isoleucine (Ile), methionine (Met), proline (Pro), phenylalanine (Phe), tryptophan (Trp) and tyrosine (Tyr)
  With negative charge, or acids: aspartic acid (Asp) and glutamic acid (Glu).
  With positive charge, or basic: lysine (Lys), arginine (Arg) and histidine (His).

The term "covalently bonded peptides" refers to peptides between which there is a covalent bond and there the bond can occur with or without spacers.

DESCRIPTION OF THE FIGURES

FIG. 4. This figure shows reactivity graphs, measured in optical densities (OD$_{492}$), of peptides derived from the α and β chains of fibrin for a sample of 33 serums from patients with RA.

FIG. 6. Analysis of ROC curve (A) and of the reactivity of the peptides p22, p22sc and p22lc to autoantibodies (B, C and D) for a set of patients with RA or psoriatic arthritis (PsA). A) The sensitivity and the specificity was calculated for all potential cut-off values and represented as ROC curve (n=111 RA positive patients, n=82 PsA positive patients). Graphs B, C and D show the reactivity of p22, p22sc and p22lc to the antibodies of RA and PsA patients (CONTROL), represented with the optimum cut-off values obtained from the analysis with the ROC curves of each assay.

FIG. 7. Analysis of ROC curve (A) and of reactivity to antibodies (B, C, D and E) of the linear peptide of β-fibrin (p38), of the linear peptide of α-fibrin (p22), of the chimeric polypeptide p38-GGG-p22) and of the mixture of p38 and p22 for a set of patients with RA or PsA. A) The sensitivity and the specificity was calculated for all potential cut-off values and represented as ROC curve (n=111 RA positive patients, n=82 PsA positive patients). Graphs B, C D and E show the reactivity of p38, p22, p38-GGG-p22 and p38+p22 to the autoantibodies of patients with RA or PsA (CONTROL), represented with the optimum cut-off values obtained from the analysis with the ROC curves of each assay.

FIG. 8. Analysis of ROC curve and of the reactivity cyclic peptides derived from filaggrin (cfc1cyc) (Pérez, T. et al. J. Pept. Sci. (2006) 12 (4), 267-278.) and the chimeric polypeptide (p18-cfc1cyc) in a set of patients with RA or PsA. A) The sensitivity and the specificity was calculated for all potential cut-off values and represented as ROC curve (n=111 RA patients, n=82 PsA patients). B) Graphs B, C show the reactivity of cfc1 and p18-cfc1cyc to the autoantibodies of patients with RA or PsA (CONTROL), represented with the optimum cut-off values obtained from the analysis with the ROC curves of each assay.

DETAILED EXPLANATION OF THE EMBODIMENTS

Figure 1:
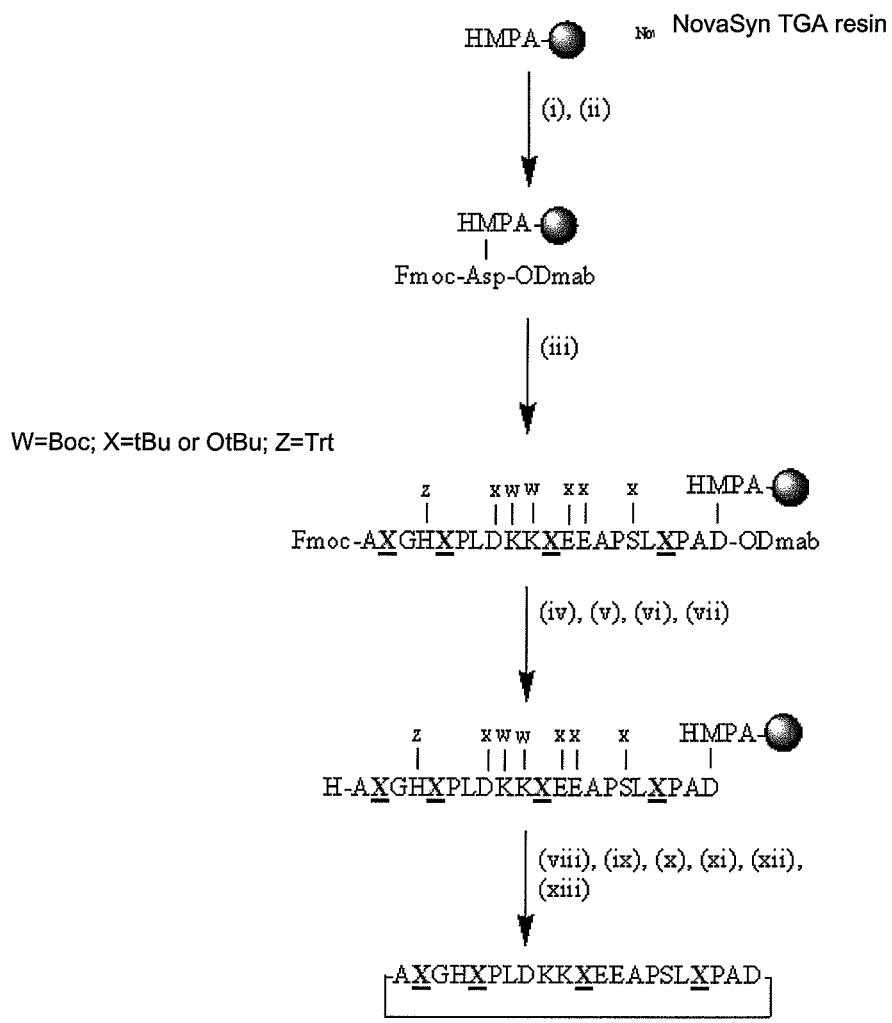
FIG. 1. This figure shows a scheme of the solid phase synthesis strategy of the "head to tail" cyclic peptide (p38HT) from the β chain of fibrin (fragment 43-62). Reagents and conditions: (i) Fmoc-Asp-Odmab DCM, DIPCDI, 20 min 0° C.; (ii) DMAP (4-Dimethylamino pyridine), DMF, 3 h; (iii) Solid phase peptide synthesis (SPPS); (iv) 20% piperidine/DMF; (v) 3% hydrazine/DMF; (vi) 20% H2O/DMF, 16 h; (vii) DMF, DCM, Methanol; (viii) 1% DIPEA/DMF; (ix) 1% HOBt/DMF (x) PyBOP/DMF, DCM, 72 h; (xi) 1% DIEA/DMF; (xii) DMF/MeOH; (xiii) TFA (trifluoroacetic acid)/EDTA/TIS (triisopropylsilane)/H$_2$O, 3 h. The groups W, X and Z are protector groups used to direct the chemical synthesis reaction of the peptides.

Below, the materials and methods are presented which were used for the development of the present invention, as well as their examples of embodiment. Said examples do not limit the invention, but their purpose is to illustrate it, revealing the sensitivity and specificity of the chimeric polypeptides and peptides of the invention.

Material and Methods

Peptide Synthesis

The synthesis of the peptides belonging to the α and β chains of the fibrin protein, with different degree of deimination (Table 1a-b), were carried out through a peptide synthesis process in solid phase using a Tentagel RAM resin (Rapp Polymere GmbH, Germany) (100 mg, 0.28 meq/g). The synthesis was carried out in a semi-automatic peptide synthesizer (SAM, Multisyntech, Germany) and the sequences were obtained in the form of C-terminal carboxamides. A Fmoc/tBut strategy was followed and the coupling reactions between amino acids were carried out in duplicate, using as condensation agents 1-hydroxybenzotriazole (HOBt) and N,N'-diisopropylcarbodiimide (DIPCDI), and concentrations three times higher than the previous. The deprotection stage of the Fmoc protector group was also was carried in duplicate using piperidine (20%) in dimethylformamide (DMF) during 10 minutes.

TABLE 1a

Sequences of the peptides derived from α-fibrin

| Name | Peptide | Sequence | SEQ ID NO |
|------|---------|----------|-----------|
| p1 | αfib (185-202) | S R A L A R E V D L K D Y E D Q Q K | 10 |
| p2 | [Cit$^{190}$] αfib (185-202) | S R A L A X E V D L K D Y E D Q Q K | 11 |
| p3 | [Cit$^{186,190}$]αfib (185-202) | S X A L A X E V D L K D Y E D Q Q K | 12 |
| p4 | [Cit$^{186}$] αfib (185-202) | S X A L A R E V D L K D Y E D Q Q K | 13 |
| p5 | αfib (208-225) | I A K D L L P S R D R Q H L P L I K | 14 |
| p6 | [Cit$^{218}$] αfib (208-225) | I A K D L L P S R D X Q H L P L I K | 15 |
| p7 | [Cit$^{216,218}$]αfib (208-225) | I A K D L L P S X D X Q H L P L I K | 16 |
| p8 | [Cit$^{216}$] αfib (208-225) | I A K D L L P S X D R Q H L P L I K | 17 |

TABLE 1a-continued

Sequences of the peptides derived from α-fibrin

| Name | Peptide | Sequence | SEQ ID NO |
|---|---|---|---|
| p9 | αfib(418-435) | G N V S P G T R R E Y H T E K L V T | 18 |
| p10 | [Cit$^{426}$]αfib(418-435) | G N V S P G T R X E Y H T E K L V T | 19 |
| p11 | [Cit$^{425,426}$]αfib(418-435) | G N V S P G T X X E Y H T E K L V T | 20 |
| p12 | [Cit$^{425}$]αfib(418-435) | G N V S P G T X R E Y H T E K L V T | 21 |
| p13 | αfib(501-518) | S G I G T L D G F R H R H P D E A A | 22 |
| p14 | [Cit$^{512}$]αfib(501-518) | S G I G T L D G F R H X H P D E A A | 23 |
| p15 | [Cit$^{510}$]αfib(501-518) | S G I G T L D G F X H R H P D E A A | 24 |
| p16 | [Cit$^{510,512}$]αfib(501-518) | S G I G T L D G F X H X H P D E A A | 25 |
| p17 | αfib(617-631) | H S T K R G H A K S R P V R G | 8 |
| p18 | [Cit$^{630}$]αfib(617-631) | H S T K R G H A K S R P V X G | 2 |
| p19 | [Cit$^{627,630}$]αfib(617-631) | H S T K R G H A K S X P V X G | 3 |
| p20 | [Cit$^{627}$]αfib(617-631) | H S T K R G H A K S X P V R G | 26 |
| p21 | [Cit$^{621}$]αfib(617-631) | H S T K X G H A K S R P V R G | 27 |
| p22 | [Cit$^{621,630}$]αfib(617-631) | H S T K X G H A K S R P V X G | 4 |
| p23 | [Cit$^{621,627}$]αfib(617-631) | H S T K X G H A K S X P V R G | 28 |
| p24 | [Cit$^{621,627,630}$]αfib(617-631) | H S T K X G H A K S X P V X G | 29 |

TABLE 1b

Sequences of the peptides derived from β-fibrin

| Name | Peptide | Sequence | SEQ ID NO |
|---|---|---|---|
| p25 | βfib(4-57) | F F S A R G H R P L D K K R E E A P | 30 |
| p26 | [Cit$^{53}$]βfib(40-57) | F F S A R G H R P L D K K X E E A P | 31 |
| p27 | [Cit$^{47}$]βfib(40-57) | F F S A R G H X P L D K K R E E A P | 32 |
| p28 | [Cit$^{47,53}$]βfib(40-57) | F F S A R G H X P L D K K X E E A P | 33 |
| p29 | [Cit$^{44,47,53}$]βfib(40-57) | F F S A X G H X P L D K K X E E A P | 34 |
| p30 | [Cit$^{44,47}$]βfib(40-57) | F F S A X G H X P L D K K R E E A P | 35 |
| p31 | [Cit$^{44,53}$]βfib(40-57) | F F S A X G H R P L D K K X E E A P | 36 |
| p32 | [Cit$^{44}$]βfib(40-57) | F F S A X G H R P L D K K R E E A P | 37 |
| p33 | βfib(43-62) | A R G H R P L D K K R E E A P S L R P A | 9 |
| p34 | [Cit$^{60}$]βfib(43-62) | A R G H R P L D K K R E E A P S L X P A | 38 |
| p35 | [Cit$^{53}$]βfib(43-62) | A R G H R P L D K K X E E A P S L R P A | 39 |
| p36 | [Cit$^{53,60}$]βfib(43-62) | A R G H R P L D K K X E E A P S L X P A | 40 |

TABLE 1b-continued

Sequences of the peptides derived from β-fibrin

| Name | Peptide | Sequence | SEQ ID NO |
|------|---------|----------|-----------|
| p37 | [Cit$^{47,53,60}$]βfib(43-62) | A R G H X P L D K K X E E A P S L X P A | 41 |
| p38 | [Cit$^{47,60}$]βfib(43-62) | A R G H X P L D K K R E E A P S L X P A | 5 |
| p39 | [Cit$^{47,53}$]βfib(43-62) | A R G H X P L D K K X E E A P S L R P A | 42 |
| p40 | [Cit$^{47}$]βfib(43-62) | A R G H X P L D K K R E E A P S L R P A | 43 |
| p41 | [Cit$^{44,47,53,60}$]βfib(43-62) | A X G H X P L D K K X E E A P S L X P A | 44 |
| p42 | [Cit$^{44,47,53}$]βfib(43-62) | A X G H X P L D K K X E E A P S L R P A | 45 |
| p43 | [Cit$^{44,47,60}$]βfib(43-62) | A X G H X P L D K K R E E A P S L X P A | 46 |
| p44 | [Cit$^{44,47}$]βfib(43-62) | A X G H X P L D K K R E E A P S L R P A | 47 |
| p45 | [Cit$^{44,53,60}$]βfib(43-62) | A X G H R P L D K K X E E A P S L X P A | 48 |
| p46 | [Cit$^{44}$]βfib(43-62) | A X G H R P L D K K R E E A P S L R P A | 49 |
| p47 | [Cit$^{44,53}$]βfib(43-62) | A X G H R P L D K K X E E A P S L R P A | 50 |
| p48 | [Cit$^{44,60}$]βfib(43-62) | A X G H R P L D K K R E E A P S L X P A | 51 |
| p49 | βfib(72-89) | R A R P A K A A A T Q K K V E R K A | 52 |
| p50 | [Cit$^{87}$]βfib(72-89) | R A R P A K A A A T Q K K V E X K A | 53 |
| P51 | [Cit$^{74}$]βfib(72-89) | R A X P A K A A A T Q K K V E R K A | 54 |
| p52 | [Cit$^{74,87}$]βfib(72-89) | R A X P A K A A A T Q K K V E X K A | 55 |
| p53 | [Cit$^{72,74,87}$]βfib(72-89) | X A X P A K A A A T Q K K V E X K A | 56 |
| p54 | [Cit$^{72,74}$]βfib(72-89) | X A X P A K A A A T Q K K V E R K A | 57 |
| p55 | [Cit$^{72,87}$]βfib(72-89) | X A R P A K A A A T Q K K V E X K A | 58 |
| p56 | [Cit$^{72}$]βfib(72-89) | X A R P A K A A A T Q K K V E R K A | 59 |
| p57 | βfib(151-168) | L K D L W Q K R Q K Q V K D N E N V | 60 |
| p58 | [Cit$^{158}$]βfib(151-168) | L K D L W Q K X Q K Q V K D N E N V | 61 |
| p59 | βfib(365-383) | ANKYQISVNKYRGTAGNAL | 62 |
| p60 | [Cit$^{376}$]βfib(365-383) | ANKYQISVNKYXGTAGNAL | 63 |
| p61 | βfib(365-390) | ANKYQISVNKYRGTAGNALMDGASQL | 64 |
| p62 | [Cit$^{376}$]βfib(365-390) | ANKYQISVNKYXGTAGNALMDGASQL | 65 |
| p63 | βfib(367-396) | KYQISVNKYRGTAGNALMDGASQLMGENRT | 66 |
| p64 | [Cit$^{395}$]βfib(367-396) | KYQISVNKYRGTAGNALMDGASQLMGENXT | 67 |
| p65 | [Cit$^{376}$]βfib(367-396) | KYQISVNKYXGTAGNALMDGASQLMGENRT | 68 |
| p66 | [Cit$^{376,395}$]βfib(367-396) | KYQISVNKYXGTAGNALMDGASQLMGENXT | 69 |
| p67 | βfib(373-390) | NKYRGTAGNALMDGASQL | 70 |
| p68 | [Cit$^{376}$]βfib(373-390) | NKYXGTAGNALMDGASQL | 71 |
| p69 | βfib(373-390)* | NKYRGTAGNALMDGASQL | 70 |
| p70 | [Cit$^{376}$]βfib(373-390)* | NKYXGTAGNALMDGASQL | 72 |
| p71 | palm-βfib(373-390) | palm-NKYRGTAGNALMDGASQL | 70 |
| p72 | palm-[Cit$^{376}$]βfib(373-390) | palm-NKYXGTAGNALMDGASQL | 72 |

Citrulline = X
*acidic peptides

The peptides were deprotected and simultaneously detached from the resin in a single stage using a mixture of trifluoroacetic acid (TFA)/triisopropylsilane (TIS)/H2O (95/2.5/2.5). The peptides were precipitated with cold diethyl ether, they were centrifuged and liophilized in 10% acetic acid. The peptides thus obtained were analysed by analytic HPLC at 215 nm. Their identity was confirmed by MALDI-TOF mass spectrometry.

Cycling of Peptides

To obtain the "head to tail" cyclic peptide p38HT whose sequence is indicated in Table 2, a standard protection of the amino acids was used. p38HT was obtained by manual synthesis in a Novasyn® TGA resin (Novabiochem Ltd., Switzerland) (0.25 mmol/g) in the form of C-terminal acid, following the procedure indicated in FIG. 1. The resin is commercially supplied functionalized with hydroxymethylphenoxyacetic acid (HMPA). The first stage consisted of the acylation of the resin with the anhydrous isomer of Fmoc-Asp-ODmab via its lateral chain. The peptide synthesis was continued following a standard Fmoc/tBut strategy. After completing the peptide synthesis, the Fmoc terminal group was eliminated with 20% piperidine in DMF. The elimination of the Dmab group was carried out by treatment with 3% hydrazine in DMF, followed by treatment with 20% water in DMF.

The deprotected resin was treated with 1% DIPEA-DMF followed by 1% HOBt-DMF. The macrocycling reaction was carried out in the resin using 3 equivalents of PyBOP at ambient temperature for 72 hours. Finally, the peptide resin was released from the peptide by acid treatment with a mixture of TFA/1,2-ethanedithiol (EDT)/TIS/H2O (95/2/1/2).

The cyclic construction was isolated by precipitation with cold diethyl ether, dissolving the final residue in 10% acetic acid and this finally being liophilized. The crude peptide was purified by reverse phase HPLC and it was identified by electrospray mass spectrometry (ES-MS).

Figure 2:
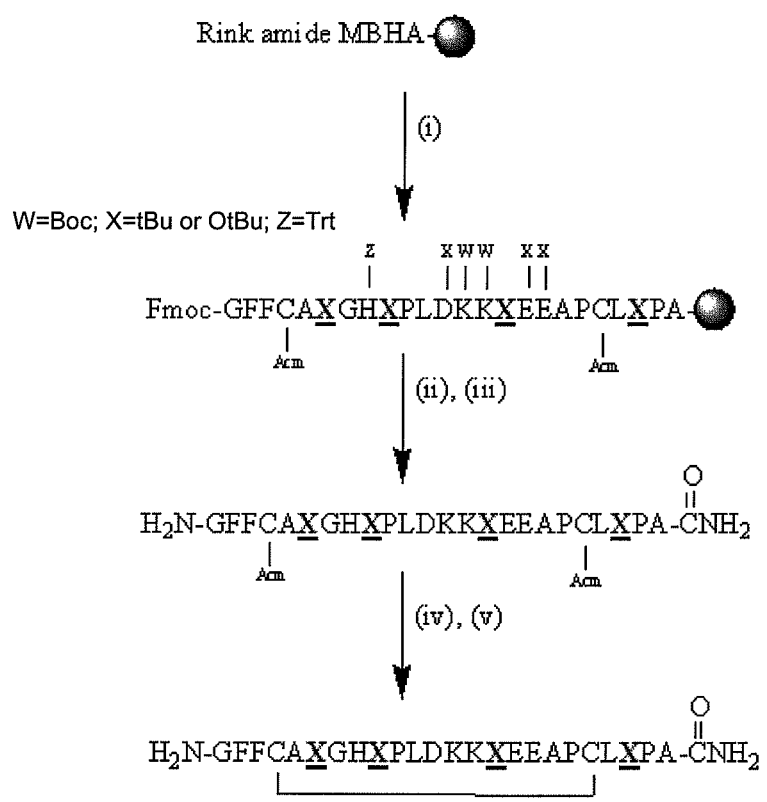
FIG. 2. This figure shows a scheme of the strategy of solid phase peptide synthesis of the cyclic peptide with disulfide bridge (p38SS). Reagents and conditions: (i) SPPS; (ii) 20% piperidine/DMF; (iii) TFA/EDT/TIS/H$_2$O, 3 h; (iv) I$_2$/MeOH, 60 min, I$_2$/MeOH 90 min; (v) DCM. The groups W, X, and Z are protector groups used to direct the peptide synthesis reaction.

To obtain the cyclic peptides in the form of disulfide, which are shown in Tables 2 and 3 (p38SS, p18-sc, p19-sc, p22-sc, p18-lc, p19-lc and p22-lc), it was necessary to substitute two serine residues from the original peptide sequence by two protected cysteine residues as Cys(Acm). The corresponding linear peptides were synthesized in the form of C-terminal carboxamides as described previously and, finally, they were released from the resin by treatment with TFA/EDT/H2O (95/2.5/2.5) and they were precipitated with cold diethyl ether. Finally, they were dissolved in 10% acetic acid and they were liophilized. The characterization of the resulting peptides was carried out by MALDI-TOF and analytic HPLC. The cycling was carried out by dissolving the peptides in acetic acid and adding a solution of iodine in methanol, to obtain the disulfide bond. After 60 minutes of stirring, water was added to accelerate the release of the Acm protector group. The resulting solution was stirred for a further 90 minutes and finally the iodine was extracted with dichloromethane. The aqueous phase was diluted three times with water and it was liophilized. The crude peptides were characterized by analytic HPLC and they were finally purified by preparative HPLC and characterized by ES-MS. FIG. 2 illustrates the synthetic procedure followed for the preparation of one of the cyclic peptides with disulfide bridges (p38SS).

TABLE 2

Cycled peptides of β fibrin

| Name | sequence | |
|---|---|---|
| p38HT | ┌─A R G H X P L D K K R E E A P S L X P A D─┐ | SEQ ID NO: 73 |
| p38SS | G F F C A R G H X P L D K K R E E A P C L X P A | SEQ ID NO: 74 |

TABLE 3

α fibrin peptide

| Name | sequence | |
|---|---|---|
| p18-sc | H C T K R G H A K C R P V X G | SEQ ID NO: 75 |
| p19-sc | H C T K R G H A K C X P V X G | SEQ ID NO: 76 |
| p22-sc | H C T K X G H A K C R P V X G | SEQ ID NO: 77 |
| p18-lc | H C T K R G H A K S R P V X G I H T C P L | SEQ ID NO: 78 |
| p19-lc | H C T K R G H A K S X P V X G I H T C P L | SEQ ID NO: 79 |
| p22-lc | H C T K X G H A K S R P V X G I H T C P L | SEQ ID NO: 80 |

Chimeric Peptides

To carry out the synthesis of the linear chimeric peptides which contain three glycine residues among the peptides selected from α- and β-fibrin (Table 4a), the aforementioned general procedure was followed.

Figure 3:
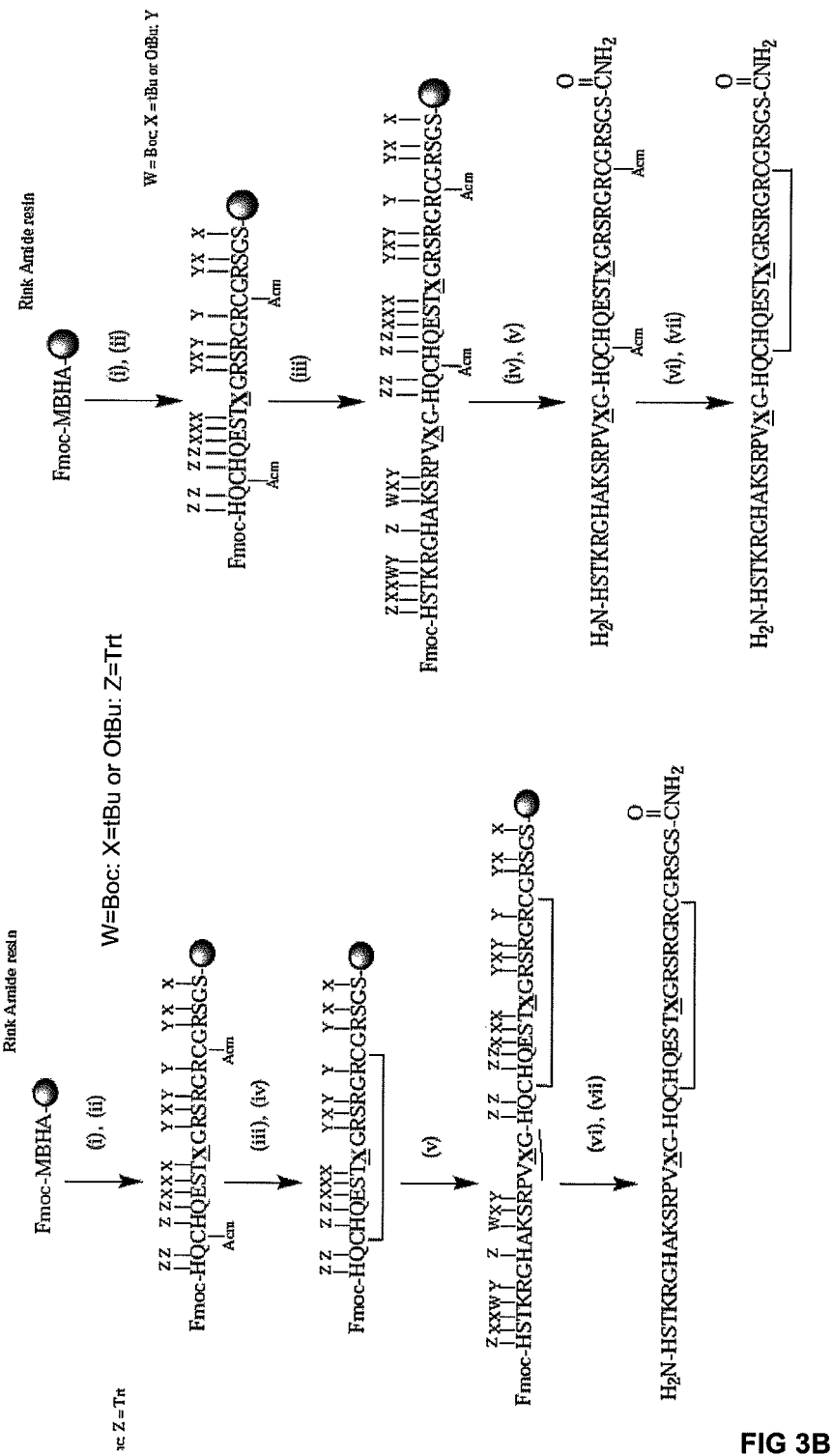
FIG. 3. This figure shows a scheme of the strategy of solid phase peptide synthesis of the peptide p18-cfc1cyc. Reagents and conditions: a) (i) 20% piperidine/DMF; (ii) SPPS of the peptide cfc1cyc; (iii) SPPS, peptide synthesis in solid phase of the peptide p18; (iv) 20% piperidine/DMF; (v) TFA/EDT/TIS/H$_2$O; (vi) I$_2$/Methanol, 60 min and H2O, 90 min; (vii) DCM b) Reagents and conditions: (i) 20% piperidine/DMF; (ii) SPPS of the peptide cfc1cyc; (iii) I$_2$/Methanol/DCM, 4 h; (iv) DMF/Methanol; (v) SPPS of p18 (vi) 20% piperidine/DMF; (vii) TFA/TIS/H$_2$O (90:5:5)

To carry out the synthesis of the α-fibrin-filaggrin chimeric (poly)peptide (p18-cfc1cyc) whose primary sequence is indicated in Table 4b, two different synthetic strategies were used. The first (FIG. 3a) consisted of the synthesis of the linear chimeric sequence in solid phase and its later cycling in solution, by the formation of a disulfide bridge. In the second strategy (FIG. 3b), the cycling of the region corresponding to the filaggrin peptide was carried out in solid phase and then, on the peptidyl resin with the filaggrin peptide already cycled, the sequence synthesis was completed with the sequence corresponding to α-fibrin. The detachment and final deprotection of the chimeric polypeptide was carried out preserving the already formed disulfide bond.

TABLE 4

Chimeric polypeptides
4a) α-fibrin-β-fibrin
4b) α-fibrin-filaggrin

| Name | sequence |
|---|---|
| (a) | |
| p38-GGG-p18 (SEQ ID NO: 81) | ARGHXPLDKKREEAPSLXPAGGGHSTKRGHAKSRPVXG |
| p38-GGG-p19 (SEQ ID NO: 82) | ARGHXPLDKKREEAPSLXPAGGGHSTKRGHAKSXPVXG |
| p38-GGG-p22 (SEQ ID NO: 83) | ARGHXPLDKKREEAPSLXPAGGGHSTKXGHAKSRPVXG |
| (b) | |
| p18-cfc1cyc (SEQ ID NO: 6) | HSTKRGHAKSRPVXGHQCHQESTXGRSRGRCGRSGS |

Serum Samples

The serum samples analysed came from patients from the Rheumatology Service of the Hospital Clínico de Barcelona. A total of 193 serum samples were worked with, of which 111 corresponded to patients diagnosed with RA, according to the revised criteria of the American Association of Rheumatology of 1987 (now American College of Rheumatology). The samples were previously tested with ELISA with the kit with CCP-2 antibodies (Immunoscan RA; Eurodiagnostica, distributed by Diasorin, Madrid, Spain) to discover the presence or absence of anti-CCP-2 antibodies. The 82 remaining serums were obtained by patients diagnosed with PsA, not preselected, and they were used as negative control.

ELISA Assays

The peptide sequences were covalently bonded to ELISA titer plates (Costar Corp., DNA-bind N-oxysuccinimide surface, Cambridge, Mass.), as previously described (Pérez, T.; Gómez, et al. *Lett. Peptide Sci.* 2002, 9, 291-300).

Briefly, the peptides were diluted to a concentration of 10 mg/mL in 0.05 M carbonate/bicarbonate buffer (pH 9.6). 100 μL of peptide solution were added to each well of the microtiter plate and it was incubated all night at 4° C. Each plate contained control wells that included all the reagents except the serum sample, to estimate the background noise, and wells that included all reagents except the peptide, to thus evaluate the non-specific serum reactions. In the controls, the wells were blocked with 2 mg BSA/well. After the incubation, the plates were blocked with 2% BSA in 0.05 M carbonate/bicarbonate buffer (pH 9.6) for 1 hour at room temperature. The serums were diluted 200 times in RIA buffer (1% BSA, 350 mM NaCl, 10 mM Tris-HCl, pH 7.6, 1% vol/vol Triton X-100, 0.5% wt/vol Na-deoxycholate, 0.1% SDS) supplemented with 10% fetal bovine serum. 100 μL/well were added and they were incubated for 1.5 hours at room temperature. After performing six washes with PBS/0.05% Tween-20, 100 μL/well of anti-human IgG conjugated to peroxidase were added, diluted 1:1000 in RIA buffer. After 1 hour of incubation at room temperature, the plates were washed six times with PBS/0.05% Tween-20 and the bound antibodies were detected with o-phenylenediamine dihydrochloride (OPD, Sigma Chemical Company) and 0.8 mL/mL of 30% hydrogen peroxide. The plates were incubated at room temperature for 30 minutes. The reaction was detained with 50 mL of 2 N $H_2SO_4$ and the absorbance values obtained were measured at a wavelength of 492 nm. All the serums were tested in duplicate. Control serums were also included to monitor the inter- and intra-assay variations.

The ELISA assays carried out with the lipopeptide p66 or with the physical mixtures of fibrin peptides, were carried out after the passive absorption of the sequences to the solid surface (Maxisorp, 96F Nunc, Roskilde, Denmark), following the methodology already described (Gomara, M. J. et al *J Immunol Methods* 2000, 234 (1-2), 23-34). The peptide p65 was analysed using Covalink NH plates (Nunc, Roskilde, Denmark), which permit the covalent bonding of the peptides through their C-terminal region. The general procedure was the following:

A 10 μg/mL peptide solution was prepared in distilled water which contained sulfo-N-hydroxysuccinimide (sulfo-NHS) at 8 mM concentration. 100 μL of the peptide/sulfo-NHS solution were added to each well. Likewise, a 2% solution of BSA/sulfo-NHS were prepared to add to the control well. The covalent reaction was started after the addition of 50 μL of a 16 mM solution of 1-ethyl-3(3-dimethylaminopropyl)-carbodiimide (EDC) to each well. The plates were incubated during the night at room temperature and the rest of the ELISA assay was carried out following the aforementioned procedure for the Costar plates.

Statistical Analysis

The statistical analysis was carried out with the statistical programme SPSS version 12.0. To establish the sensitivity/specificity of the different ELISA assays in the different pathologies, a ROC curve study was carried out. To compare proportions, the Chi-square test or the Fischer test were used and for the bivariant analysis of the continuous variables the Student t-test and or Wilcoxon-Mann-Whitney assay were used. For multiple comparisons, the variance analysis or the Kruskal-Wallis test was used. To apply the parametric tests, normality contrasts (Kolmogorov-Smirnov) and homocedasticity tests (Levene test) were previously performed.

EXAMPLES OF EMBODIMENT OF THE INVENTION

Example 1

Identification of Epitopes of α-Fibrin and β-Fibrin

With the object of detecting those peptides of the fibrin protein that were more reactive to positive serums for RA (hereinafter RA serums), the influence of the degree of deimination was analysed by the synthesis of peptides derived from fibrin with different arginine/citrulline ratio. The identification of the regions of the α-fibrin and β-fibrin chains that would be used in the assays was carried out by predictions of antigenicity made by computer. The Hopp and Woods hydrophilia scales, of Janin accessibility and Welling antigenicity were used. Furthermore, it was taken into consideration what regions had a greater probability of forming beta turns and which, therefore, should be located in a more external zone of the protein, having with this a greater facility for interacting with the antibodies. The peptides were finally synthesized in solid phase and characterized by their sequence, HPLC and MALDI-T of mass spectrometry.

These peptides were assayed by immunoassay (ELISA) to determine their capacity to recognize autoantibodies present in positive serums for RA. To identify what peptides were the best substrate for the autoantibodies all the synthesized peptides were initially tested with 33 positive serums for RA and with 40 control serums. As shown in FIG. 4, a considerable increase in the sensitivity of peptides p18, p19 and p22 derived from the α-fibrin chain was observed, where the arginine had been substituted in position 630. Although p24 also has a citrulline in this specific position, it is a totally citrullinated version of region 617-631. In accordance with the previous results of the inventors of the present invention, a positive net charge could be an additional factor which contributed to the reactivity of the peptide. According to the experience of the inventors, a suitable balance of Arg/Cit residues in the peptides may favour a formation with greater binding capacity to the autoantibodies, which has been favourable for improving their analytical, diagnostic and prognostic use.

The other peptides corresponding to region 617-631 of the α-fibrin with an unmodified arginine in the same position showed less reactivity. For the peptides derived from the β-fibrin chain, of those obtained from the region defined between positions 43-62, p38 was the one which offered the best absorbency results ($DO_{492}$), i.e. a greater bonding to the autoantibodies.

Example 2

Detection Tests of Autoantibodies by Cycled Peptides

Cycled Peptides of the β-Fibrin.

From region 43-62 of β-fibrin, the peptides derived from said region were cycled to determine if this treatment, cycling, managed to increase its affinity for antibodies. Thus, two versions of cyclic peptides from region 43-62 of the β-fibrin (Table 2) were prepared. The first of these versions, p38HT (head to tail), corresponds to cycled peptide p38, which was obtained in solid phase by the formation of an amide bond between the N-terminal end of the peptide and the carboxyl group of an Asp residue introduced in the C-terminal end of the sequence of the peptide protected by the Odmab group (4[N-[1-(4,4-dimethyl-2,6-dioxo-cyclohexylidene)-3-methylbutylamino)benzyloxy) (FIG. 1). The second version of the peptides prepared, p38SS, was obtained by substitution of two serine residues by two cysteines in the 43-62 region of the β-fibrin and the cycling was carried out by oxidation in the iodine/methanol solution (FIG. 2).

Figure 5:
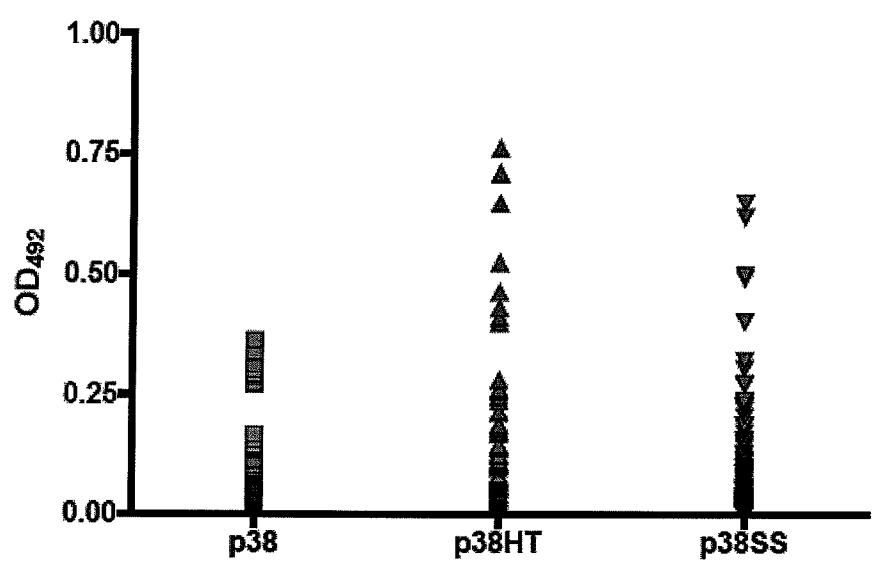
FIG. 5. This figure shows reactivity graphs, measured in optical densities (OD$_{492}$), of peptides derived from the β chain of fibrin p38 and the cyclic peptides p38HT and p38SS for a sample of 110 RA serums.

The two versions of cycled peptides was tested by ELISA with 110 positive serums for RA and 80 control serums. As shown in FIG. 5, the capacity of the linear peptides to detect autoantibodies was significantly exceeded by the cyclic peptides ($p<0.05$), although between p38HT and p38SS the differences were not significant ($p=162$).

Cycled Peptides of α-Fibrin.

As with the β-fibrin, cycled peptides derived from α-fibrin were derived from those that had offered higher antigenicity values, p18, p19 and p22. In this way, two cycled versions of each one of the peptides were prepared, a large one and another short one, as indicated in Table 3, and they were tested with 110 positive serums for RA and 70 positive serums for PsA. The ROC curve analysis showed greater area under the curve (AUC) values for the short cyclic peptides (0.829, 0.745 and 0.703 for p18-sc, p19-sc and p22-sc respectively) in comparison with the large one (0.738, 0.703, 0.685 for p18-lc, p19-lc and p22-lc respectively). As shown in FIG. 6, the higher AUC and sensitivity ($p=0.008$) values were obtained for the peptide p22-sc, when the size of the cycling ring was smaller.

On the other hand, we should highlight that the fibrin peptides used in the assays did not give rise to false positives with positive samples for PsA, unlike what happens with other RA detection methods. Consequently, and as described by various authors (21, 22), who state that the antibodies detected in the anti-CCP test are more frequently populations affected by PsA, the cycled peptides of α-fibrin described in this section may be of great relevance for improving RA detection systems.

Example 3

Detection Tests of RA Autoantibodies by α-Fibrin-β-Fibrin and Fibrin-Filaggrin Chimeric Peptides From the specificity and selectivity data obtained for the different regions of the polypeptides derived from α-fibrin and β-fibrin chimeric peptides were designed and synthesized in solid phase (Table 4).

The ELISA analysis showed that the α-fibrin and β-fibrin chimeric polypeptides analysed by ROC curves offered moderately higher AUC values than those corresponding to monomeric peptides (FIG. 7). Surprisingly, when the same assays were carried out with fibrin-filaggrin chimeric polypeptides, where the filaggrin peptide is cycled, the results of sensitivity and specificity were better.

To prepare this last assay, two peptides were prepared: cfc1cyc, belonging to the group of peptides known as CCP-1 (15), and p18-cfc1cyc, resulting from the covalent bond of the first with p18. The ratio between the sensitivity and specificity of both peptides is present in FIG. 8. The sensitivity of the ELISA with p18-cfc1cyc was 82%, significantly higher than that reached by the ELISA with cfc1cyc (65.8%; p=0.002). The specificity was very high in both cases (93%). This high sensitivity without loss of specificity is fairly relevant bearing in mind that the group used as control consisted of patients affected by PsA, an inflammatory disease with clinical symptoms that may simulate RA. On the other hand, the frequency of antibodies against the polypeptide p18-cfc1cyc (6%) in the control population (PsA) is similar to that described by other authors that use the commercial test based on CCP-2, having reported a prevalence of 5.6-7.8%

Example 4

Detection Tests of Chimeric Polypeptide RA Antibodies by Mixtures of Peptides

In order to improve RA detection methods based on peptides derived from fibrin, different mixtures thereof were prepared.

A panel of 23 serum samples were used for which the commercial test based on CCP-2 had offered negative results and their reactivity to different peptide mixtures chosen from those that had been antigenically more relevant was studied (Table 5). These peptide mixtures were only capable of detecting 4 of the 23 positive RA samples. However, the chimeric polypeptide p18-cfc1cyc was capable of detecting RA autoantibodies in 8 serums, therefore reaching a reactivity of 33% at maximums of 21% and 17% obtained with other methods tested. These results demonstrated that the fibrin-filaggrin chimeric peptides are capable of improving the sensitivity of the methods of detection of RA.

TABLE 5

| Serum sample | p38* | p18cfc1cyc** | α-fib + β-fib + cfc1cyc |
|---|---|---|---|
| 1 | + | + | − |
| 2 | − | − | − |
| 3 | + | − | − |
| 4 | − | − | − |
| 5 | − | − | − |
| 6 | − | + | − |
| 7 | − | − | + |
| 8 | − | + | + |
| 9 | − | + | + |
| 10 | − | + | + |
| 11 | − | − | − |
| 12 | − | + | − |
| 13 | − | − | − |
| 14 | − | − | − |
| 15 | − | − | − |
| 16 | − | − | − |
| 17 | − | − | − |
| 18 | − | − | − |
| 19 | + | + | − |
| 20 | − | + | − |
| 21 | − | − | − |
| 22 | + | − | − |
| 23 | − | − | − |
| | (4/23) 17% | (8/23) 34.8% | (4/23) 17% |

*p38: peptide derived from β-fibrin
**p18cfc1cyc: α-fibrin-filaggrin chimeric polypeptide It is important to mention that the fibrin-filaggrin chimeric polypeptides and, more particularly, the polypeptide p18-cfc1cyc, have been capable of offering results with greater sensitivity than those of cfc1cyc and even of detecting positive serums for RA where the commercial CCP-2 test offered false negatives. Indeed, over 46% of the negative serums for the CCP-2 test reacted with p18-cfc1cyc and/or p38, indicating that the peptides derived from fibrin and the fibrin-filaggrin chimeric polypeptides can permit the development of RA autoantibody detection tests with better results than the tests prior to the present invention.

Figure 9:
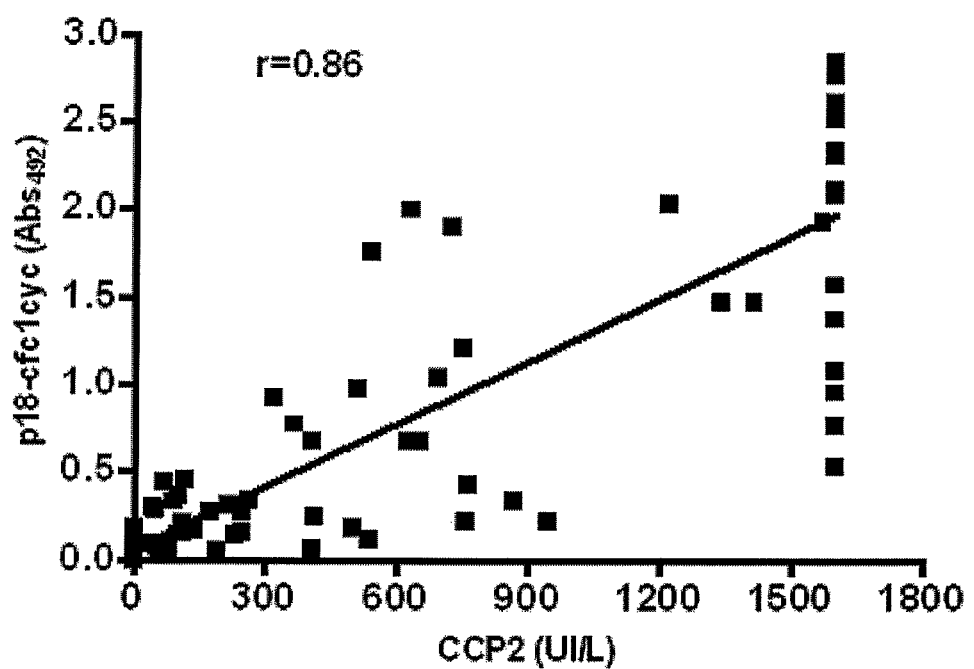
FIG. 9. Analysis of the correlation between the titers of anti-peptide antibodies p18-cfc1cyc and anti-CCP-2.

During the execution of these assays it was even verified that there was the existence of a correlation between p18-cfc1cyc and CCP-2, as shown in FIG. 9 (r=0.86, p<0.001). These results reinforce the use of the fibrin-filaggrin peptides for strengthening the diagnosis and prognosis methods of RA.

Example 5

Sensitivity and Specificity Diagnosis of the Anti-CCP2 Antibodies and Citrullinated Chimeric Antipeptides (Fibrin/Filaggrin) (fb/f (Fibrin/Filaggrin) Anti-Chimerics)

To carry out this analysis, the values of the anti-CCP2 and fb/f anti-chimeric (p18, p19, p22) antibodies were used using the ELISA technique. Therefore, patients with rheumatoid arthritis (RA) were used (ACR criteria, 1987) (n=322) and controls from the blood bank of the Hospital Clínico (n=307) in order to evaluate their sensitivity, specificity and positive and negative predictive value to diagnose RA. To do this, a ROC curve analysis was carried out which demonstrated with a specificity of 98%, the following cut-off values for the different antigens:

| | |
|---|---|
| Anti-CCP2: | 29 IU/l |
| fb/f anti-chimeric-p18: | 0.241 |
| Fb/f anti-chimeric-p19: | 0.229 |
| Fb/f anti-chimeric-p22: | 0.280 |

Below, the ROC curves are detailed for RA diagnosis between populations with RA (n=322) and control population from the blood bank (n=307).

TABLE 6

ROC curve for anti CCP2

| | | |
|---|---|---|
| Sensitivity | 238/322 | 73.91% |
| Specificity | 301/307 | 98.05% |
| Positive predictive value | 238/244 | 97.54% |
| Negative predictive value | 301/385 | 78.18% |

Figure 10:
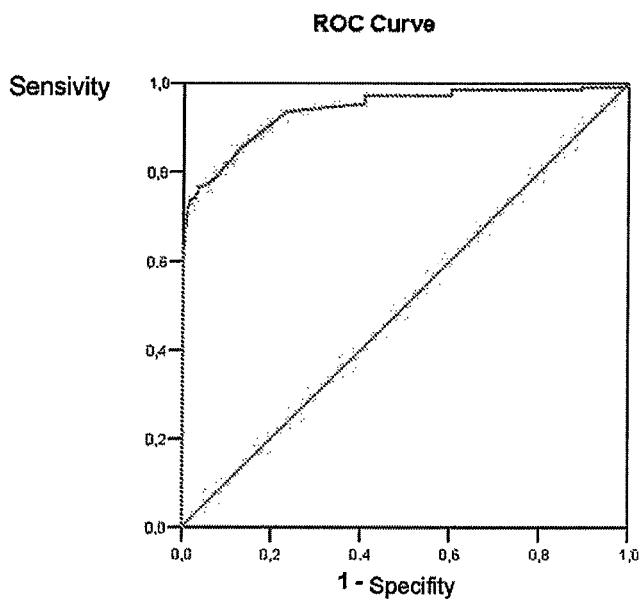
FIG. 10. ROC curve for Anti-CCP-2

See FIG. 10

TABLE 7

ROC curve for fb/f anti-chimeric-p18

| | | |
|---|---|---|
| Sensitivity | 232/322 | 72.05% |
| Specificity | 301/307 | 98.05% |
| Positive predictive value | 232/238 | 97.48% |
| Negative predictive value | 301/391 | 76.98% |

Figure 11:
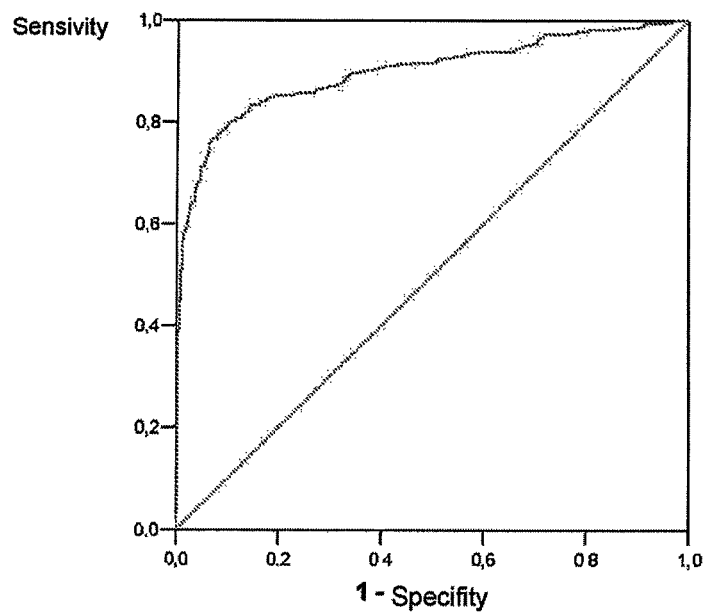
FIG. 11. ROC curve for fibrin/filaggrin anti-chimeric p-18

See FIG. 11

TABLE 8

| ROC curve for fb/f anti-chimeric-p19 | | |
| --- | --- | --- |
| Sensitivity | 251/322 | 77.95% |
| Specificity | 301/307 | 98.05% |
| Positive predictive value | 251/257 | 97.67% |
| Negative predictive value | 301/372 | 80.91% |

Figure 12:
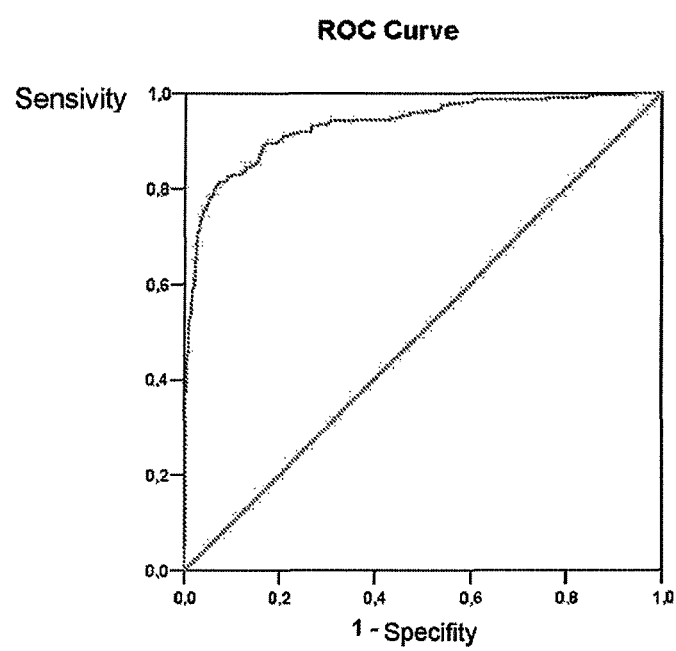
FIG. 12. ROC curve for fibrin/filaggrin anti-chimeric p-19

See FIG. 12

TABLE 9

| ROC curve for fb/f anti-chimeric-p22 | | |
| --- | --- | --- |
| Sensitivity | 230/322 | 71.43% |
| Specificity | 303/307 | 98.70% |
| Positive predictive value | 230/234 | 98.29% |
| Negative predictive value | 303/395 | 76.71% |

Figure 13:
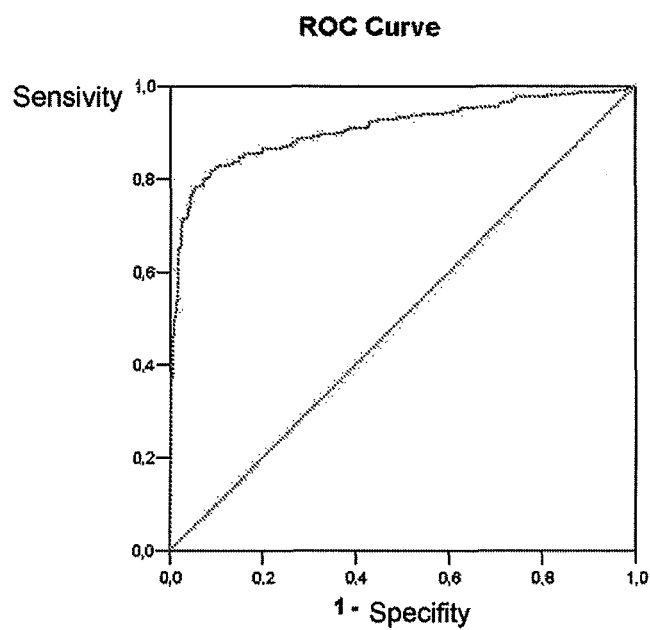
FIG. 13. ROC curve for fibrin/filaggrin anti-chimeric p-22
Figure 14:
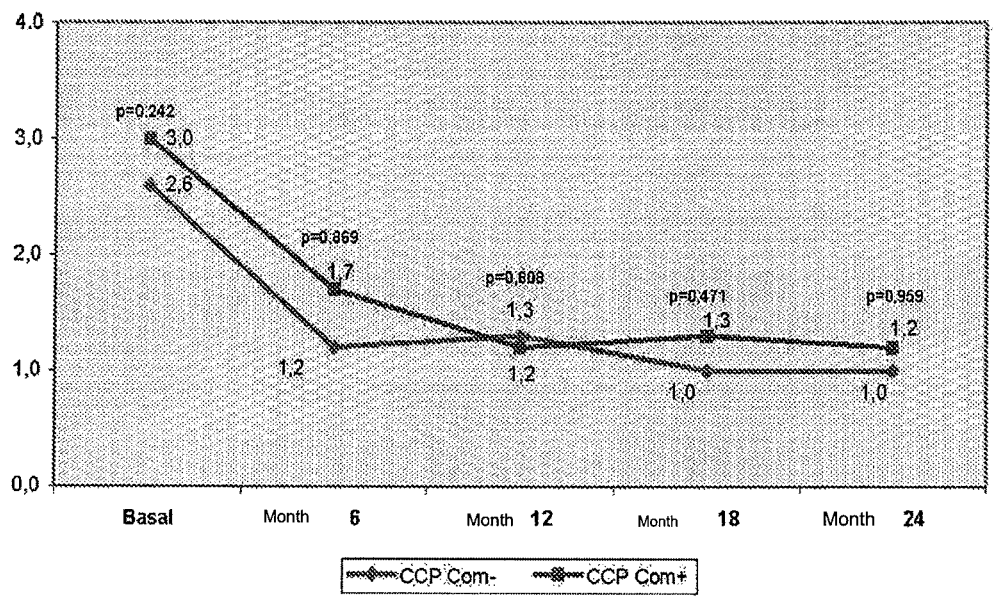
FIG. 14. Evolution of the values of the C-reactive protein (CRP) throughout the monitoring between CCP-2 (+) and (−) patients.
Figure 15:
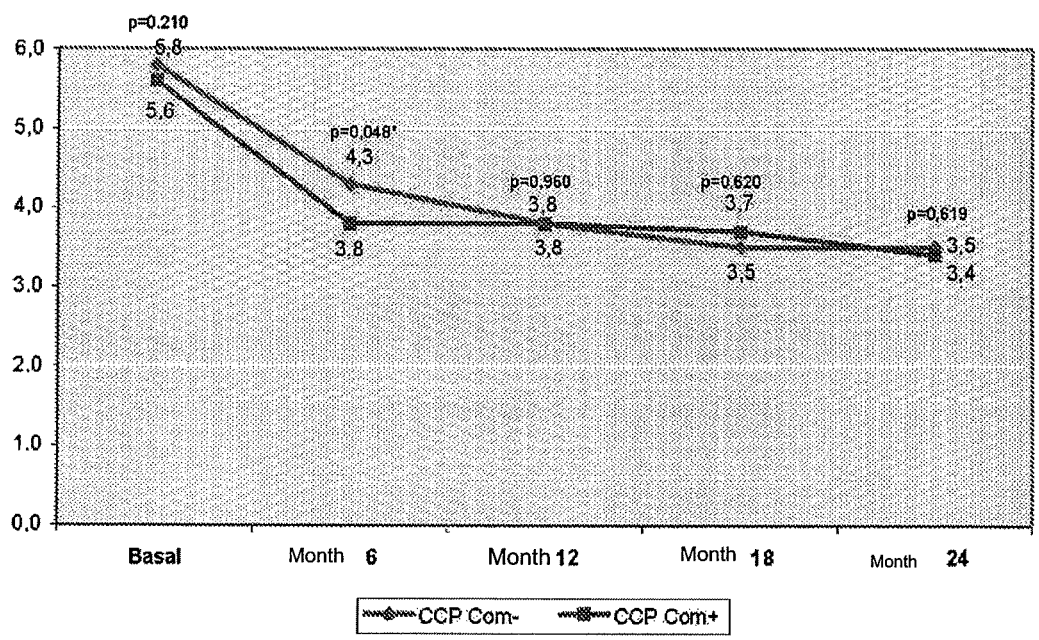
FIG. 15. Evolution of the DAS28 activity index throughout the monitoring between CCP-2 (+) and (−) patients.
Figure 16:
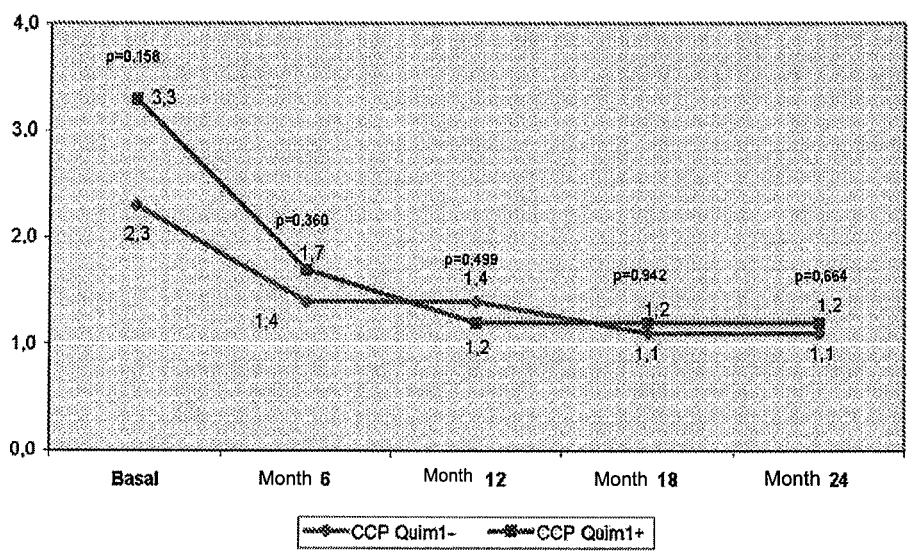
FIG. 16. Evolution of the values of the C-reactive protein (CRP) throughout the monitoring between patients with anti-p-18 (+) and (−) anti-chimerics.
Figure 17:
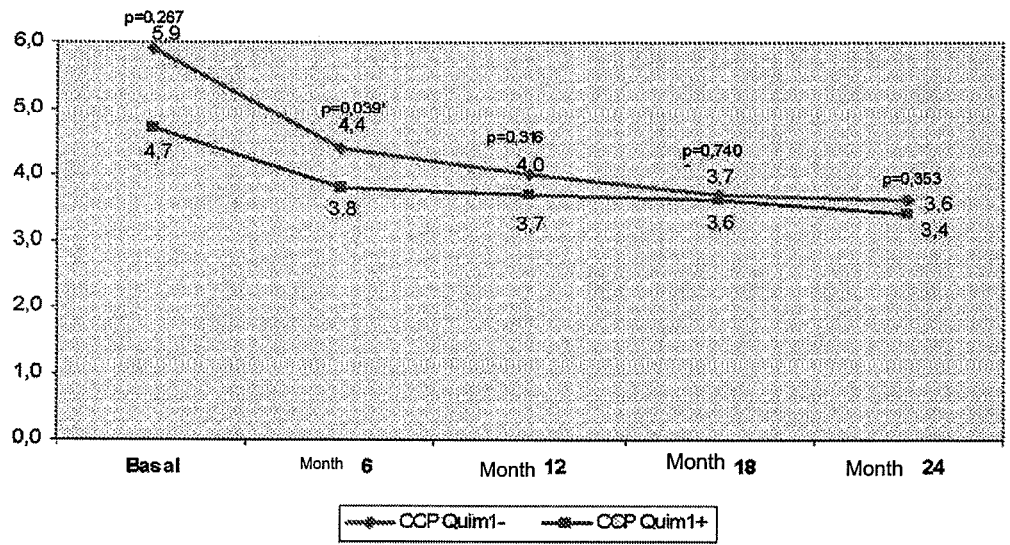
FIG. 17. Evolution of the DAS28 activity index throughout the monitoring between patients with anti-p-18 (+) and (−) anti-chimerics.

See FIG. 13

With this assay, it is again demonstrated that in the serum of patients with RA there are antibodies that react against citrullinated fibrin/filaggrin chimeric peptides, reinforcing the idea that the epitopes of the alpha chain of human fibrin, present in the rheumatoid synovial, could be constituted by the main antigens which trigger the immune response with the formation of these autoantibodies, in patients with RA.

In the sensitivity/specificity analysis of these antibodies, it has been demonstrated that they have a high sensitivity and specificity for the diagnosis of RA. Indeed, using a population of 322 patients with RA and 307 control (blood bank) and maintaining a 98% specificity, the sensitivity of the three fibrin/filaggrin (fb/f) chimeric peptides (p18, p19, p22) was 72%, 78% and 71% respectively, a sensitivity similar to that observed with the commercial anti-CCP-2 (74%). Interestingly, and although the correlation between the different antibodies is very close, there is a considerable percentage of discrepancies between them (between 13-15% of discordant serums), which reveals that the determination of more than one antibody increases the sensitivity (up to 81%) without practically losing specificity (96-97%).

Indeed, a relatively important number of patients has been observed with non-concordant values. 13.9% of patients have discrepancies in the positivity of the CCP-2 antibody and the fb/f anti-chimeric p-18.

TABLE 10

| | fb/f chimeric-p18− | fb/f chimeric-p18+ | Total |
| --- | --- | --- | --- |
| CCP-2− | 22 | 8 | 30 |
| CCP-2+ | 6 | 65 | 71 |

When the analysis was carried out between anti-CCP-2 and the antibodies against fb/f chimeric peptides p-19 and p-22, discrepancies of 13.3% and 15.3% respectively, are also observed. Even between the three fb/f chimeric antibodies, the discrepancy level is also 13.9%, with a greater number of positive discrepant serums for fb/b chimeric antibodies, as illustrated in Table 11:

TABLE 11

| | fb/f− chimerics | fb/f+ chimerics | Total |
| --- | --- | --- | --- |
| CCP2− | 18 | 12 | 30 |
| CCP2+ | 2 | 69 | 71 |

Example 6

Sensitivity/Specificity of the Antibodies to Citrullinated Peptides (CCP-2 and fb/f chimerics) in Different Pathologies Later, and using the cut-off points to define the positivity through ROC curves between patients with RA and the control group of the blood bank, serums of patients of three different studies have been studied:
1. Systemic lupus erythematous (SLE): n=119
2. Psoriatic arthritis: (PsA): n=133
3. Chronic hepatitis C virus (HCV): n=84

The sensitivity or positivity of the different antibodies is very low in the three pathologies, which in accordance with Table 12, demonstrates the specificity of the four antibodies used and their value in the diagnosis of RA. In said table the data referring to the specificity of the anti-CCP-2 and fb/f anti-chimeric p18 antibodies are shown

TABLE 12

| | Anti CCP2 | Anti-chimeric fb/f-p18 |
| --- | --- | --- |
| SLE | 110/119 (92.4%) | 109/119 (91.6%)P |
| psoriatic arthritis | 129/133 (98%) | 130/133 (97.7%) |
| Chronic hepatitis C virus | 82/84 (97.6%) | 82/84 (97.6%) |

As can be verified in the table, the specificity is very high (97-98%), both with the anti-CCP-2 and in the chimerics in the psoriatic arthritis pathologies and chronic hepatitis C virus, with very few false positive cases.

Therefore, in this specificity study of the different autoantibodies in other pathologies where autoimmune phenomena are observed (Systemic lupus erythematous, chronic hepatitis C) or which have clinical symptoms similar to RA (psoriatic arthritis), it is clearly verified that the fb/f anti-chimeric antibodies are extremely specific.

Example 7

Prognostic Significance

The objective of this analysis was to analyse the prognostic value of the citrullinated antibodies derived from human fibrin domains in RA and to compare it with what are determined in clinical practice with the second generation commercial kit (CCP2, Eurodiagnostica). As has been seen throughout the present invention, the peptides which have demonstrated a greater sensitivity/specificity balance are the fb/f chimerics p18, p19 and p22; it is for this reason that they are the ones that have been used for the study of their prognostic significance.

To carry out the present analysis 118 patients have been studied with RA of over two years evolution and which, after starting a therapeutic protocol with anti-rheumatic drugs, have been under monitoring for two years. The degree of joint destruction (radiological progression) at the end of the two years of monitoring has been taken as main trigger measure. It has been possible to verify that different clinical, biological and immunogenetic variables have been associated to a greater joint destruction, among them the presence of specific antibodies to citrullinated cyclic peptides. Especially in the case of the anti-CCP-2 and the fb/f chimeric p18 antibodies, its presence at the baseline time has been more clearly associated to a greater radiological lesion after two years of monitoring.

However, is very important to highlight that those negative anti CCP-2 patients but positive for the anti-chimerics, showed a degree of joint destruction similar to the positive antiCCP, demonstrating that these antibodies may give additional prognostic information.

Below, the data obtained to reach the already commented conclusions is provided. In first place, the different characteristics of the patients analysed is provided:

| | |
|---|---|
| Women (%) | 82.2 |
| Age (years), ± S.D. | 53.8 ± 15 |
| Disease duration (months), X ± S.D. | 10 ± 6.7 |
| EAV pain (mm), X ± S.D | 50.6 ± 21 |
| VGPatient (mm), X ± S.D. | 57.6 ± 15.8 |
| VGMedium (mm), X ± S.D. | 55.7 ± 14 |
| NAD28, X ± S.D. | 9.8 ± 5.5 |
| NAI28, X ± S.D. | 8.1 ± 4.2 |
| DAS 28, X ± S.D. | 5.7 ± 0.9 |
| DAS 28 > 5.1 (%) | 75.4 |
| mHAQ, X ± S.D. | 0.9 ± 0.5 |
| VSG (mm/h), X ± S.D. | 39.7 ± 24.4 |
| CRP (mm/dL), X ± S.D. | 2.8 ± 2.3 |
| Haemoglobin (mg/dL), X ± S.D. | 12.7 ± 1.4 |
| Positive rheumatoid factor (>25U) | 73.7 |
| Positive anti-CCP-2 (>50 U) (%) | 69.7 |
| Rheumatoid epitope (%) | 72.5 |
| Homozygote rheumatoid epitope (%) | 19.3 |
| HLA-DRB1-04 (%) | 44.5 |

As regards the detection of specific antibodies to citrullinated synthetic chimeric peptides in this assay (fb/f anti-chimerics) (ELISA), the results were the following:

TABLE 13

| | |
|---|---|
| Fb/f chimeric-p18 (=112) | 72.3% |
| Fb/f chimeric-p19 (n = 109) | 75.5% |
| Fb/f chimeric-p22 (n = 109) | 73.5% |

In the Table 14 it is possible to observe the values of the radiological damage (baseline and after two years) in accordance with the presence or absence of the different specific autoantibodies to the citrullinated peptides.

As has already been mentioned to assess the prognostic value of the different variables when predicting joint destruction, the presence of progression of the destruction was catalogued, when at the end of the monitoring (24 months) there was an increase in the Larsen value greater than or equal to 4 points (between month 0 and month 24). Following this criteria, 39 of the 118 patients (33%) had progression of joint destruction and 79 (67%) did not.

On the other hand, the bivariant analysis of the three antibodies against citrullinated chimeric peptides (anti-chimerics) gave rise to the results stated in Table 15.

TABLE 15

| Anti-chimeric peptides | No progression | progression | P value |
|---|---|---|---|
| Fb/f chimeric-p18+ | 65.7% | 85.3% | 0.037 |
| Fb/f chimeric-p19+ | 70.8% | 84.8% | 0.126 |
| Fb/f chimeric-p22+ | 69.2% | 81.8% | 0.182 |

These results demonstrated that the proportion of patients with antibodies against citrullinated fibrin/filaggrin chimeric peptides is higher in patients with radiological progression than in patients who do not have it. Furthermore, if we pay attention to the results already stated in example 5 when the radiological progression data between positive and negative antiCCP-2 patients (with positive or negative fb/b anti-chimerics) is analysed, it is observed how the behaviour of group CCP-2-/chimeric+ is similar to group CCP-2+ (i.e. with greater radiological progression) and not to group CCP-2-. This indicates that the presence of these antibodies determines a greater radiological progression, also in negative antiCCP-2 patients. Hence, the importance in the diagnosis and the prognosis of the disease of the use of the chimeric peptides of the present invention.

Therefore, it can be verified based on these data, how the antibodies against citrullinated cyclic peptides, especially the anti CCP-2 and the fb/f chimeric p18 antibodies, are associated to a greater joint destruction and how their presence at the baseline time is associated to a greater radiological lesion after two hours of monitoring.

Example 8

Analysis of the Association Between Antibodies Against Citrullinated Peptides and HLADRB Genotype In Table 16 we can observe the frequency of the different DRB04 and DRB03 alleles, as well as the rheumatoid epitope in patients with specific antibodies to citrullinated peptides.

TABLE 14

| | CCP-2+ (n = 74) | CCP-2− (n = 35) | Q-p18+ (n = 84) | Q-p18− (n = 17) | Q-p19+ (n = 80) | Q-p19− (n = 18) | Q-p-22+ (n = 85) | Q-p-22− (n = 13) |
|---|---|---|---|---|---|---|---|---|
| Baseline Larsen | 1.5 ± 0.3 | 0.7 ± 0.3 | 1.6 ± 0.4* | 0.3 ± 0.2* | 1.5 ± 0.2 | 1.5 ± 0.3 | 1.5 ± 0.3 | 0.5 ± 0.3 |
| Final Larsen | 6.9 ± 1.2* | 3.5 ± 1.3 | 7 ± 1.2** | 3. ± 1.1** | 6.5 ± 1.1 | 4.3 ± 1.9 | 6.1 ± 1 | 5.4 ± 2.2 |
| Delta Larsen | 5.4 ± 1.1 | 2.8 ± 1.2 | 5.4 ± 1.1 | 2.6 ± 1.1 | 5 ± 1.8 | 3.8 ± 1.8 | 5 ± 2.2 | 4.6 ± 0.9 |

*p = 0.006;
**p = 0.022.
Delta: value of the difference between Larsen final and baseline.

TABLE 16

|  | CCP-2+ | CCP-2− | p | -fb/f- chimeric p18+ | fb/f-chimeric- p18− | p |
|---|---|---|---|---|---|---|
| DRB04 | 54.2% | 17.2% | 0.001 | 52.2% | 20.8% | 0.008 |
| DRB04 homozygote | 6.9% | 0% | NS | 5.8% | 0% | NS |
| Rheumatoid epitope | 81.9% | 48.3% | 0.001 | 78.3% | 62.5% | NS |
| Homozygote rheumatoid epitope | 25% | 3.4% | 0.012 | 23.2% | 0% | 0.009 |
| DRB03 | 11.6% | 14.3% | NS | 11.9% | 13% | NS |

Table 16 demonstrates the association between DRB04 and the antiCCP-2 and fb/f chimeric p18 antibodies.

The invention claimed is:

1. A chimeric polypeptide, which comprises at least two citrullinated peptide subunits (a) and (b), covalently bonded, each subunit having at least one arginine substituted for citrulline, whereby:
   a. the subunit (a) consists of a sequence selected from SEQ ID NO: 2, SEQ ID NO:3, and SEQ ID NO:4, and
   b. the second subunit (b) is cyclized and consists of SEQ ID NO:1 of filaggrin protein,
   wherein said chimeric polypeptide is capable of interacting with autoimmune antibodies generated during rheumatoid arthritis.

2. The chimeric polypeptide of claim 1, wherein the chimeric polypeptide is SEQ ID NO:6.

3. The chimeric polypeptide of claim 1 where said polypeptide is marked or conjugated with at least one transporting molecule.

4. A composition that comprises the chimeric polypeptide of claim 1.

5. The composition of claim 4, which further comprises the polypeptide CCP-2.

6. A method for the detection of specific autoantibodies of rheumatoid arthritis in a biological sample which comprises:
   a. placing in contact the biological sample with at least one of the chimeric polypeptides of claim 1, and
   b. detecting the interaction between the specific autoantibodies and the chimeric polypeptides or the composition of step (a).

7. The method of claim 6, wherein the biological sample comes from patients with genotype HLADRB.

8. A kit for the diagnosis or prognosis of rheumatoid arthritis which comprises at least one of the chimeric polypeptides of claim 1, and the reagents and/or buffers necessary to permit the formation of the antibody-antigen complex.

9. The kit of claim 8, which further comprises the chimeric polypeptide CCP-2.

10. A kit for the diagnosis or prognosis of rheumatoid arthritis which comprises the composition of claim 4, and the reagents and/or buffers necessary to permit the formation of the antibody-antigen complex.

* * * * *

```
                        SEQUENCE LISTING

<160> NUMBER OF SEQ ID NOS: 83

<210> SEQ ID NO 1
<211> LENGTH: 21
<212> TYPE: PRT
<213> ORGANISM: Artificial sequence
<220> FEATURE:
<223> OTHER INFORMATION: Synthesized Sequence cfc1cyc
<220> FEATURE:
<221> NAME/KEY: MISC_FEATURE
<222> LOCATION: (9)..(9)
<223> OTHER INFORMATION: X = Citrulline
<220> FEATURE:
<221> NAME/KEY: DISULFID
<222> LOCATION: (3)..(16)
<223> OTHER INFORMATION: Disulfide bridge between two cysteine amino
      acids

<400> SEQUENCE: 1

His Gln Cys His Gln Glu Ser Thr Xaa Gly Arg Ser Arg Gly Arg Cys
1               5                  10                  15

Gly Arg Ser Gly Ser

<210> SEQ ID NO 2
<211> LENGTH: 15
<212> TYPE: PRT
<213> ORGANISM: Artificial sequence
<220> FEATURE:
<223> OTHER INFORMATION: Synthesized Sequence p18
<220> FEATURE:
<221> NAME/KEY: MISC_FEATURE
<222> LOCATION: (14)..(14)
<223> OTHER INFORMATION: X = citrulline

<400> SEQUENCE: 2

His Ser Thr Lys Arg Gly His Ala Lys Ser Arg Pro Val Xaa Gly
1               5                  10                  15

<210> SEQ ID NO 3
<211> LENGTH: 15
<212> TYPE: PRT
<213> ORGANISM: Artificial sequence
<220> FEATURE:
<223> OTHER INFORMATION: Synthesized Sequence p19
<220> FEATURE:
<221> NAME/KEY: MISC_FEATURE
<222> LOCATION: (11)..(11)
<223> OTHER INFORMATION: X = citrulline
<220> FEATURE:
<221> NAME/KEY: MISC_FEATURE
<222> LOCATION: (14)..(14)
<223> OTHER INFORMATION: X = citrulline

<400> SEQUENCE: 3
```

His Ser Thr Lys Arg Gly His Ala Lys Ser Xaa Pro Val Xaa Gly
1               5                   10                  15

<210> SEQ ID NO 4
<211> LENGTH: 15
<212> TYPE: PRT
<213> ORGANISM: Artificial sequence
<220> FEATURE:
<223> OTHER INFORMATION: Synthesized Sequence p22
<220> FEATURE:
<221> NAME/KEY: MISC_FEATURE
<222> LOCATION: (5)..(5)
<223> OTHER INFORMATION: X = citrulline
<220> FEATURE:
<221> NAME/KEY: MISC_FEATURE
<222> LOCATION: (14)..(14)
<223> OTHER INFORMATION: X = citrulline

<400> SEQUENCE: 4

His Ser Thr Lys Xaa Gly His Ala Lys Ser Arg Pro Val Xaa Gly
1               5                   10                  15

<210> SEQ ID NO 5
<211> LENGTH: 20
<212> TYPE: PRT
<213> ORGANISM: Artificial sequence
<220> FEATURE:
<223> OTHER INFORMATION: Synthesized Sequence p38
<221> NAME/KEY: MISC_FEATURE
<222> LOCATION: (5)..(5)
<223> OTHER INFORMATION: X = citrulline
<220> FEATURE:
<221> NAME/KEY: MISC_FEATURE
<222> LOCATION: (18)..(18)
<223> OTHER INFORMATION: X = citrulline

<400> SEQUENCE: 5

Ala Arg Gly His Xaa Pro Leu Asp Lys Lys Arg Glu Glu Ala Pro Ser
1               5                   10                  15

Leu Xaa Pro Ala
            20

<210> SEQ ID NO 6
<211> LENGTH: 36
<212> TYPE: PRT
<213> ORGANISM: Artificial sequence
<220> FEATURE:
<223> OTHER INFORMATION: Synthesized Sequence p18-cfc1cyc
<220> FEATURE:
<221> NAME/KEY: MISC_FEATURE
<222> LOCATION: (14)..(14)
<223> OTHER INFORMATION: X = citrulline
<220> FEATURE:
<221> NAME/KEY: MISC_FEATURE
<222> LOCATION: (24)..(24)
<223> OTHER INFORMATION: X = citrulline
<220> FEATURE:
<221> NAME/KEY: DISULFID
<222> LOCATION: (18)..(31)
<223> OTHER INFORMATION: Disulfide bridge between two cysteine amino
      acids

<400> SEQUENCE: 6

His Ser Thr Lys Arg Gly His Ala Lys Ser Arg Pro Val Xaa Gly His
1               5                   10                  15

Gln Cys His Gln Glu Ser Thr Xaa Gly Arg Ser Arg Gly Arg Cys Gly
                20                  25                  30

Arg Ser Gly Ser
            35

<210> SEQ ID NO 7
<211> LENGTH: 19
<212> TYPE: PRT
<213> ORGANISM: homo sapiens
<220> FEATURE:
<221> NAME/KEY: PEPTIDE
<222> LOCATION: (1)..(19)
<223> OTHER INFORMATION: region 306-324 of filaggrin protein

<400> SEQUENCE: 7

Ser His Gln Glu Ser Thr Arg Gly Arg Ser Arg Gly Arg Ser Gly Arg
1               5                   10                  15

Ser Gly Ser

<210> SEQ ID NO 8
<211> LENGTH: 15
<212> TYPE: PRT
<213> ORGANISM: homo sapiens
<220> FEATURE:
<221> NAME/KEY: PEPTIDE
<222> LOCATION: (1)..(15)
<223> OTHER INFORMATION: region 617-631 of alpha fibrin

<400> SEQUENCE: 8

His Ser Thr Lys Arg Gly His Ala Lys Ser Arg Pro Val Arg Gly
1               5                   10                  15

<210> SEQ ID NO 9
<211> LENGTH: 20
<212> TYPE: PRT
<213> ORGANISM: homo sapiens
<220> FEATURE:
<221> NAME/KEY: PEPTIDE
<222> LOCATION: (1)..(20)
<223> OTHER INFORMATION: region 43-62 of beta fibrin

<400> SEQUENCE: 9

Ala Arg Gly His Arg Pro Leu Asp Lys Lys Arg Glu Glu Ala Pro Ser
1               5                   10                  15

Leu Arg Pro Ala
            20

<210> SEQ ID NO 10
<211> LENGTH: 18
<212> TYPE: PRT
<213> ORGANISM: Homo sapiens
<220> FEATURE:
<221> NAME/KEY: PEPTIDE
<222> LOCATION: (1)..(18)
<223> OTHER INFORMATION: Region 185-202 of alfa fibrin protein

<400> SEQUENCE: 10

Ser Arg Ala Leu Ala Arg Glu Val Asp Leu Lys Asp Tyr Glu Asp Gln
1               5                   10                  15

Gln Lys

<210> SEQ ID NO 11
<211> LENGTH: 18
<212> TYPE: PRT
<213> ORGANISM: Artificial Sequence
<220> FEATURE:
<223> OTHER INFORMATION: Modified region 185-202 of alfa fibrin protein
<220> FEATURE:
<221> NAME/KEY: MISC_FEATURE
<222> LOCATION: (6)..(6)
<223> OTHER INFORMATION: X = Citrulline

<400> SEQUENCE: 11

Ser Arg Ala Leu Ala Xaa Glu Val Asp Leu Lys Asp Tyr Glu Asp Gln
1               5                   10                  15

Gln Lys

<210> SEQ ID NO 12
<211> LENGTH: 18
<212> TYPE: PRT
<213> ORGANISM: Artificial Sequence
<220> FEATURE:
<223> OTHER INFORMATION: Modified region 185-202 of alfa fibrin protein
<220> FEATURE:
<221> NAME/KEY: MISC_FEATURE
<222> LOCATION: (2)..(2)
<223> OTHER INFORMATION: X = Citrulline
<220> FEATURE:
<221> NAME/KEY: MISC_FEATURE
<222> LOCATION: (6)..(6)
<223> OTHER INFORMATION: X = Citrulline

<400> SEQUENCE: 12

Ser Xaa Ala Leu Ala Xaa Glu Val Asp Leu Lys Asp Tyr Glu Asp Gln
1               5                   10                  15

Gln Lys

<210> SEQ ID NO 13
<211> LENGTH: 18
<212> TYPE: PRT
<213> ORGANISM: Artificial Sequence
<220> FEATURE:
<223> OTHER INFORMATION: Modified region 185-202 of alfa fibrin protein
<220> FEATURE:
<221> NAME/KEY: MISC_FEATURE
<222> LOCATION: (2)..(2)
<223> OTHER INFORMATION: X = Citrulline

<400> SEQUENCE: 13

Ser Xaa Ala Leu Ala Arg Glu Val Asp Leu Lys Asp Tyr Glu Asp Gln
1               5                   10                  15

Gln Lys

<210> SEQ ID NO 14
<211> LENGTH: 18
<212> TYPE: PRT
<213> ORGANISM: Homo sapiens
<220> FEATURE:
<221> NAME/KEY: PEPTIDE
<222> LOCATION: (1)..(18)
<223> OTHER INFORMATION: Region 208-225 of alfa fibrin

<400> SEQUENCE: 14

Ile Ala Lys Asp Leu Leu Pro Ser Arg Asp Arg Gln His Leu Pro Leu
1               5                   10                  15

Ile Lys

<210> SEQ ID NO 15
<211> LENGTH: 18
<212> TYPE: PRT
<213> ORGANISM: Artificial Sequence
<220> FEATURE:
<223> OTHER INFORMATION: Modified region 208-225 of alfa fibrin protein
<220> FEATURE:
<221> NAME/KEY: MISC_FEATURE
<222> LOCATION: (11)..(11)
<223> OTHER INFORMATION: X = Citrulline

<400> SEQUENCE: 15

```
Ile Ala Lys Asp Leu Leu Pro Ser Arg Asp Xaa Gln His Leu Pro Leu
1               5                   10                  15

Ile Lys

<210> SEQ ID NO 16
<211> LENGTH: 18
<212> TYPE: PRT
<213> ORGANISM: Artificial Sequence
<220> FEATURE:
<223> OTHER INFORMATION: Modified region 208-225 of alfa fibrin protein
<220> FEATURE:
<221> NAME/KEY: MISC_FEATURE
<222> LOCATION: (9)..(9)
<223> OTHER INFORMATION: X = Citrulline
<220> FEATURE:
<221> NAME/KEY: MISC_FEATURE
<222> LOCATION: (11)..(11)
<223> OTHER INFORMATION: X = Citrulline

<400> SEQUENCE: 16

Ile Ala Lys Asp Leu Leu Pro Ser Xaa Asp Xaa Gln His Leu Pro Leu
1               5                   10                  15

Ile Lys

<210> SEQ ID NO 17
<211> LENGTH: 18
<212> TYPE: PRT
<213> ORGANISM: Artificial Sequence
<220> FEATURE:
<223> OTHER INFORMATION: Modified region 208-225 of alfa fibrin protein
<220> FEATURE:
<221> NAME/KEY: MISC_FEATURE
<222> LOCATION: (9)..(9)
<223> OTHER INFORMATION: X = Citrulline

<400> SEQUENCE: 17

Ile Ala Lys Asp Leu Leu Pro Ser Xaa Asp Arg Gln His Leu Pro Leu
1               5                   10                  15

Ile Lys

<210> SEQ ID NO 18
<211> LENGTH: 18
<212> TYPE: PRT
<213> ORGANISM: Homo sapiens
<220> FEATURE:
<221> NAME/KEY: PEPTIDE
<222> LOCATION: (1)..(18)
<223> OTHER INFORMATION: Region 418-435 of alfa fibrin protein

<400> SEQUENCE: 18

Gly Asn Val Ser Pro Gly Thr Arg Arg Glu Tyr His Thr Glu Lys Leu
1               5                   10                  15

Val Thr

<210> SEQ ID NO 19
<211> LENGTH: 18
<212> TYPE: PRT
<213> ORGANISM: Artificial Sequence
<220> FEATURE:
<223> OTHER INFORMATION: Modified region 418-435 of alfa fibrin protein
<220> FEATURE:
<221> NAME/KEY: MISC_FEATURE
<222> LOCATION: (9)..(9)
<223> OTHER INFORMATION: X = Citrulline

<400> SEQUENCE: 19
```

```
Gly Asn Val Ser Pro Gly Thr Arg Xaa Glu Tyr His Thr Glu Lys Leu
1               5                   10                  15

Val Thr

<210> SEQ ID NO 20
<211> LENGTH: 18
<212> TYPE: PRT
<213> ORGANISM: Artificial Sequence
<220> FEATURE:
<223> OTHER INFORMATION: Modified region 418-435 of alfa fibrin protein
<220> FEATURE:
<221> NAME/KEY: MISC_FEATURE
<222> LOCATION: (8)..(8)
<223> OTHER INFORMATION: X = Citrulline
<220> FEATURE:
<221> NAME/KEY: MISC_FEATURE
<222> LOCATION: (9)..(9)
<223> OTHER INFORMATION: X = Citrulline

<400> SEQUENCE: 20

Gly Asn Val Ser Pro Gly Thr Xaa Xaa Glu Tyr His Thr Glu Lys Leu
1               5                   10                  15

Val Thr

<210> SEQ ID NO 21
<211> LENGTH: 18
<212> TYPE: PRT
<213> ORGANISM: Artificial Sequence
<220> FEATURE:
<223> OTHER INFORMATION: Modified region 418-435 of alfa fibrin protein
<220> FEATURE:
<221> NAME/KEY: MISC_FEATURE
<222> LOCATION: (8)..(8)
<223> OTHER INFORMATION: X = Citrulline

<400> SEQUENCE: 21

Gly Asn Val Ser Pro Gly Thr Xaa Arg Glu Tyr His Thr Glu Lys Leu
1               5                   10                  15

Val Thr

<210> SEQ ID NO 22
<211> LENGTH: 18
<212> TYPE: PRT
<213> ORGANISM: Homo sapiens
<220> FEATURE:
<221> NAME/KEY: PEPTIDE
<222> LOCATION: (1)..(18)
<223> OTHER INFORMATION: Region 501-518 of alfa fibrin protein

<400> SEQUENCE: 22

Ser Gly Ile Gly Thr Leu Asp Gly Phe Arg His Arg His Pro Asp Glu
1               5                   10                  15

Ala Ala

<210> SEQ ID NO 23
<211> LENGTH: 18
<212> TYPE: PRT
<213> ORGANISM: Artificial Sequence
<220> FEATURE:
<223> OTHER INFORMATION: Modified region 501-518 of alfa fibrin protein
<220> FEATURE:
<221> NAME/KEY: MISC_FEATURE
<222> LOCATION: (12)..(12)
<223> OTHER INFORMATION: X = Citrulline

<400> SEQUENCE: 23

Ser Gly Ile Gly Thr Leu Asp Gly Phe Arg His Xaa His Pro Asp Glu
```

```
1               5                   10                  15

Ala Ala

<210> SEQ ID NO 24
<211> LENGTH: 18
<212> TYPE: PRT
<213> ORGANISM: Artificial Sequence
<220> FEATURE:
<223> OTHER INFORMATION: Modified region 501-518 of alfa fibrin protein
<220> FEATURE:
<221> NAME/KEY: MISC_FEATURE
<222> LOCATION: (10)..(10)
<223> OTHER INFORMATION: X = Citrulline

<400> SEQUENCE: 24

Ser Gly Ile Gly Thr Leu Asp Gly Phe Xaa His Arg His Pro Asp Glu
1               5                   10                  15

Ala Ala

<210> SEQ ID NO 25
<211> LENGTH: 18
<212> TYPE: PRT
<213> ORGANISM: Artificial Sequence
<220> FEATURE:
<223> OTHER INFORMATION: Modified region 501-518 of alfa fibrin protein
<220> FEATURE:
<221> NAME/KEY: MISC_FEATURE
<222> LOCATION: (10)..(10)
<223> OTHER INFORMATION: X = Citrulline
<220> FEATURE:
<221> NAME/KEY: MISC_FEATURE
<222> LOCATION: (12)..(12)
<223> OTHER INFORMATION: X = Citrulline

<400> SEQUENCE: 25

Ser Gly Ile Gly Thr Leu Asp Gly Phe Xaa His Xaa His Pro Asp Glu
1               5                   10                  15

Ala Ala

<210> SEQ ID NO 26
<211> LENGTH: 15
<212> TYPE: PRT
<213> ORGANISM: Artificial Sequence
<220> FEATURE:
<223> OTHER INFORMATION: Modified region 617-631 of alfa fibrin protein
<220> FEATURE:
<221> NAME/KEY: MISC_FEATURE
<222> LOCATION: (11)..(11)
<223> OTHER INFORMATION: X = Citrulline

<400> SEQUENCE: 26

His Ser Thr Lys Arg Gly His Ala Lys Ser Xaa Pro Val Arg Gly
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: Modified region 617-631 of alfa fibrin protein
<220> FEATURE:
<221> NAME/KEY: MISC_FEATURE
<222> LOCATION: (5)..(5)
<223> OTHER INFORMATION: X = Citrulline

<400> SEQUENCE: 27

His Ser Thr Lys Xaa Gly His Ala Lys Ser Arg Pro Val Arg Gly
1               5                   10                  15
```

```
<210> SEQ ID NO 28
<211> LENGTH: 15
<212> TYPE: PRT
<213> ORGANISM: Artificial Sequence
<220> FEATURE:
<223> OTHER INFORMATION: Modified region 617-631 of alfa fibrin protein
<220> FEATURE:
<221> NAME/KEY: MISC_FEATURE
<222> LOCATION: (5)..(5)
<223> OTHER INFORMATION: X = Citrulline
<220> FEATURE:
<221> NAME/KEY: MISC_FEATURE
<222> LOCATION: (11)..(11)
<223> OTHER INFORMATION: X = Citrulline

<400> SEQUENCE: 28

His Ser Thr Lys Xaa Gly His Ala Lys Ser Xaa Pro Val Arg Gly
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: Modified region 617-631 of alfa fibrin protein
<220> FEATURE:
<221> NAME/KEY: MISC_FEATURE
<222> LOCATION: (5)..(5)
<223> OTHER INFORMATION: X = Citrulline
<220> FEATURE:
<221> NAME/KEY: MISC_FEATURE
<222> LOCATION: (11)..(11)
<223> OTHER INFORMATION: X = Citrulline
<220> FEATURE:
<221> NAME/KEY: MISC_FEATURE
<222> LOCATION: (14)..(14)
<223> OTHER INFORMATION: X = Citrulline

<400> SEQUENCE: 29

His Ser Thr Lys Xaa Gly His Ala Lys Ser Xaa Pro Val Xaa Gly
1               5                   10                  15

<210> SEQ ID NO 30
<211> LENGTH: 18
<212> TYPE: PRT
<213> ORGANISM: Homo sapiens
<220> FEATURE:
<221> NAME/KEY: PEPTIDE
<222> LOCATION: (1)..(18)
<223> OTHER INFORMATION: Region 40-57 of beta fibrin protein

<400> SEQUENCE: 30

Phe Phe Ser Ala Arg Gly His Arg Pro Leu Asp Lys Lys Arg Glu Glu
1               5                   10                  15

Ala Pro

<210> SEQ ID NO 31
<211> LENGTH: 18
<212> TYPE: PRT
<213> ORGANISM: Artificial Sequence
<220> FEATURE:
<223> OTHER INFORMATION: Modified region 40-57 of beta fibrin protein
<220> FEATURE:
<221> NAME/KEY: MISC_FEATURE
<222> LOCATION: (14)..(14)
<223> OTHER INFORMATION: X = Citrulline

<400> SEQUENCE: 31

Phe Phe Ser Ala Arg Gly His Arg Pro Leu Asp Lys Lys Xaa Glu Glu
```

<210> SEQ ID NO 32
<211> LENGTH: 18
<212> TYPE: PRT
<213> ORGANISM: Artificial Sequence
<220> FEATURE:
<223> OTHER INFORMATION: Modified region 40-57 of beta fibrin protein
<220> FEATURE:
<221> NAME/KEY: MISC_FEATURE
<222> LOCATION: (8)..(8)
<223> OTHER INFORMATION: X = Citrulline

<400> SEQUENCE: 32

```
Phe Phe Ser Ala Arg Gly His Xaa Pro Leu Asp Lys Lys Arg Glu Glu
1               5                   10                  15

Ala Pro
```

<210> SEQ ID NO 33
<211> LENGTH: 18
<212> TYPE: PRT
<213> ORGANISM: Artificial Sequence
<220> FEATURE:
<223> OTHER INFORMATION: Modified region 40-57 of beta fibrin protein
<220> FEATURE:
<221> NAME/KEY: MISC_FEATURE
<222> LOCATION: (8)..(8)
<223> OTHER INFORMATION: X = Citrulline
<220> FEATURE:
<221> NAME/KEY: MISC_FEATURE
<222> LOCATION: (14)..(14)
<223> OTHER INFORMATION: X = Citrulline

<400> SEQUENCE: 33

```
Phe Phe Ser Ala Arg Gly His Xaa Pro Leu Asp Lys Lys Xaa Glu Glu
1               5                   10                  15

Ala Pro
```

<210> SEQ ID NO 34
<211> LENGTH: 18
<212> TYPE: PRT
<213> ORGANISM: Artificial Sequence
<220> FEATURE:
<223> OTHER INFORMATION: Modified region 40-57 of beta fibrin protein
<220> FEATURE:
<221> NAME/KEY: MISC_FEATURE
<222> LOCATION: (5)..(5)
<223> OTHER INFORMATION: X = Citrulline
<220> FEATURE:
<221> NAME/KEY: MISC_FEATURE
<222> LOCATION: (8)..(8)
<223> OTHER INFORMATION: X = Citrulline
<220> FEATURE:
<221> NAME/KEY: MISC_FEATURE
<222> LOCATION: (14)..(14)
<223> OTHER INFORMATION: X = Citrulline

<400> SEQUENCE: 34

```
Phe Phe Ser Ala Xaa Gly His Xaa Pro Leu Asp Lys Lys Xaa Glu Glu
1               5                   10                  15

Ala Pro
```

<210> SEQ ID NO 35
<211> LENGTH: 18
<212> TYPE: PRT
<213> ORGANISM: Artificial Sequence
<220> FEATURE:

```
<223> OTHER INFORMATION: Modified region 40-57 of beta fibrin protein
<220> FEATURE:
<221> NAME/KEY: MISC_FEATURE
<222> LOCATION: (5)..(5)
<223> OTHER INFORMATION: X = Citrulline
<220> FEATURE:
<221> NAME/KEY: MISC_FEATURE
<222> LOCATION: (8)..(8)
<223> OTHER INFORMATION: X = Citrulline

<400> SEQUENCE: 35

Phe Phe Ser Ala Xaa Gly His Xaa Pro Leu Asp Lys Lys Arg Glu Glu
1               5                   10                  15

Ala Pro

<210> SEQ ID NO 36
<211> LENGTH: 18
<212> TYPE: PRT
<213> ORGANISM: Artificial Sequence
<220> FEATURE:
<223> OTHER INFORMATION: Modified region 40-57 of beta fibrin protein
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (14)..(14)
<223> OTHER INFORMATION: X = Citrulline

<400> SEQUENCE: 36

Phe Phe Ser Ala Xaa Gly His Arg Pro Leu Asp Lys Lys Xaa Glu Glu
1               5                   10                  15

Ala Pro

<210> SEQ ID NO 37
<211> LENGTH: 18
<212> TYPE: PRT
<213> ORGANISM: Artificial Sequence
<220> FEATURE:
<223> OTHER INFORMATION: Modified region 40-57 of beta fibrin protein
<220> FEATURE:
<221> NAME/KEY: MISC_FEATURE
<222> LOCATION: (5)..(5)
<223> OTHER INFORMATION: X = Citrulline

<400> SEQUENCE: 37

Phe Phe Ser Ala Xaa Gly His Arg Pro Leu Asp Lys Lys Arg Glu Glu
1               5                   10                  15

Ala Pro

<210> SEQ ID NO 38
<211> LENGTH: 20
<212> TYPE: PRT
<213> ORGANISM: Artificial Sequence
<220> FEATURE:
<223> OTHER INFORMATION: Modified region 43-62 of beta fibrin protein
<220> FEATURE:
<221> NAME/KEY: MISC_FEATURE
<222> LOCATION: (18)..(18)
<223> OTHER INFORMATION: X = Citrulline

<400> SEQUENCE: 38

Ala Arg Gly His Arg Pro Leu Asp Lys Lys Arg Glu Glu Ala Pro Ser
1               5                   10                  15

Leu Xaa Pro Ala
            20
```

```
<210> SEQ ID NO 39
<211> LENGTH: 20
<212> TYPE: PRT
<213> ORGANISM: Artificial Sequence
<220> FEATURE:
<223> OTHER INFORMATION: Modified region 43-62 of beta fibrin protein
<220> FEATURE:
<221> NAME/KEY: MISC_FEATURE
<222> LOCATION: (11)..(11)
<223> OTHER INFORMATION: X = Citrulline

<400> SEQUENCE: 39

Ala Arg Gly His Arg Pro Leu Asp Lys Lys Xaa Glu Glu Ala Pro Ser
1               5                   10                  15

Leu Arg Pro Ala
            20

<210> SEQ ID NO 40
<211> LENGTH: 20
<212> TYPE: PRT
<213> ORGANISM: Artificial Sequence
<220> FEATURE:
<223> OTHER INFORMATION: Modified region 43-62 of beta fibrin protein
<220> FEATURE:
<221> NAME/KEY: MISC_FEATURE
<222> LOCATION: (11)..(11)
<223> OTHER INFORMATION: X = Citrulline
<220> FEATURE:
<221> NAME/KEY: MISC_FEATURE
<222> LOCATION: (18)..(18)
<223> OTHER INFORMATION: X = Citrulline

<400> SEQUENCE: 40

Ala Arg Gly His Arg Pro Leu Asp Lys Lys Xaa Glu Glu Ala Pro Ser
1               5                   10                  15

Leu Xaa Pro Ala
            20

<210> SEQ ID NO 41
<211> LENGTH: 20
<212> TYPE: PRT
<213> ORGANISM: Artificial Sequence
<220> FEATURE:
<223> OTHER INFORMATION: Modified region 43-62 of beta fibrin protein
<220> FEATURE:
<221> NAME/KEY: MISC_FEATURE
<222> LOCATION: (5)..(5)
<223> OTHER INFORMATION: X = Citrulline
<220> FEATURE:
<221> NAME/KEY: MISC_FEATURE
<222> LOCATION: (11)..(11)
<223> OTHER INFORMATION: X = Citrulline
<220> FEATURE:
<221> NAME/KEY: MISC_FEATURE
<222> LOCATION: (18)..(18)
<223> OTHER INFORMATION: X = Citrulline

<400> SEQUENCE: 41

Ala Arg Gly His Xaa Pro Leu Asp Lys Lys Xaa Glu Glu Ala Pro Ser
1               5                   10                  15

Leu Xaa Pro Ala
            20

<210> SEQ ID NO 42
<211> LENGTH: 20
<212> TYPE: PRT
<213> ORGANISM: Artificial Sequence
<220> FEATURE:
<223> OTHER INFORMATION: Modified region 43-62 of beta fibrin protein
```

```
-continued

<220> FEATURE:
<221> NAME/KEY: MISC_FEATURE
<222> LOCATION: (5)..(5)
<223> OTHER INFORMATION: X = Citrulline
<220> FEATURE:
<221> NAME/KEY: MISC_FEATURE
<222> LOCATION: (11)..(11)
<223> OTHER INFORMATION: X = Citrulline

<400> SEQUENCE: 42

Ala Arg Gly His Xaa Pro Leu Asp Lys Lys Xaa Glu Glu Ala Pro Ser
1               5                   10                  15

Leu Arg Pro Ala
            20

<210> SEQ ID NO 43
<211> LENGTH: 20
<212> TYPE: PRT
<213> ORGANISM: Artificial Sequence
<220> FEATURE:
<223> OTHER INFORMATION: Modified region 43-62 of beta fibrin protein
<220> FEATURE:
<221> NAME/KEY: MISC_FEATURE
<222> LOCATION: (5)..(5)
<223> OTHER INFORMATION: X = Citrulline

<400> SEQUENCE: 43

Ala Arg Gly His Xaa Pro Leu Asp Lys Lys Arg Glu Glu Ala Pro Ser
1               5                   10                  15

Leu Arg Pro Ala
            20

<210> SEQ ID NO 44
<211> LENGTH: 20
<212> TYPE: PRT
<213> ORGANISM: Artificial Sequence
<220> FEATURE:
<223> OTHER INFORMATION: Modified region 43-62 of beta fibrin protein
<220> FEATURE:
<221> NAME/KEY: MISC_FEATURE
<222> LOCATION: (2)..(2)
<223> OTHER INFORMATION: X = Citrulline
<220> FEATURE:
<221> NAME/KEY: MISC_FEATURE
<222> LOCATION: (5)..(5)
<223> OTHER INFORMATION: X = Citrulline
<220> FEATURE:
<221> NAME/KEY: MISC_FEATURE
<222> LOCATION: (11)..(11)
<223> OTHER INFORMATION: X = Citrulline
<220> FEATURE:
<221> NAME/KEY: MISC_FEATURE
<222> LOCATION: (18)..(18)
<223> OTHER INFORMATION: X = Citrulline

<400> SEQUENCE: 44

Ala Xaa Gly His Xaa Pro Leu Asp Lys Lys Xaa Glu Glu Ala Pro Ser
1               5                   10                  15

Leu Xaa Pro Ala
            20

<210> SEQ ID NO 45
<211> LENGTH: 20
<212> TYPE: PRT
<213> ORGANISM: Artificial Sequence
<220> FEATURE:
<223> OTHER INFORMATION: Modified region 43-62 of beta fibrin protein
<220> FEATURE:
<221> NAME/KEY: MISC_FEATURE
<222> LOCATION: (2)..(2)
```

```
<223> OTHER INFORMATION: X = Citrulline
<220> FEATURE:
<221> NAME/KEY: MISC_FEATURE
<222> LOCATION: (5)..(5)
<223> OTHER INFORMATION: X = Citrulline
<220> FEATURE:
<221> NAME/KEY: MISC_FEATURE
<222> LOCATION: (11)..(11)
<223> OTHER INFORMATION: X = Citrulline

<400> SEQUENCE: 45

Ala Xaa Gly His Xaa Pro Leu Asp Lys Lys Xaa Glu Glu Ala Pro Ser
1               5                   10                  15

Leu Arg Pro Ala
            20

<210> SEQ ID NO 46
<211> LENGTH: 20
<212> TYPE: PRT
<213> ORGANISM: Artificial Sequence
<220> FEATURE:
<223> OTHER INFORMATION: Modified region 43-62 of beta fibrin protein
<220> FEATURE:
<221> NAME/KEY: MISC_FEATURE
<222> LOCATION: (2)..(2)
<223> OTHER INFORMATION: X = Citrulline
<220> FEATURE:
<221> NAME/KEY: MISC_FEATURE
<222> LOCATION: (5)..(5)
<223> OTHER INFORMATION: X = Citrulline
<220> FEATURE:
<221> NAME/KEY: MISC_FEATURE
<222> LOCATION: (18)..(18)
<223> OTHER INFORMATION: X = Citrulline

<400> SEQUENCE: 46

Ala Xaa Gly His Xaa Pro Leu Asp Lys Lys Arg Glu Glu Ala Pro Ser
1               5                   10                  15

Leu Xaa Pro Ala
            20

<210> SEQ ID NO 47
<211> LENGTH: 20
<212> TYPE: PRT
<213> ORGANISM: Artificial Sequence
<220> FEATURE:
<223> OTHER INFORMATION: Modified region 43-62 of beta fibrin protein
<220> FEATURE:
<221> NAME/KEY: MISC_FEATURE
<222> LOCATION: (2)..(2)
<223> OTHER INFORMATION: X = Citrulline
<220> FEATURE:
<221> NAME/KEY: MISC_FEATURE
<222> LOCATION: (5)..(5)
<223> OTHER INFORMATION: X = Citrulline

<400> SEQUENCE: 47

Ala Xaa Gly His Xaa Pro Leu Asp Lys Lys Arg Glu Glu Ala Pro Ser
1               5                   10                  15

Leu Arg Pro Ala
            20

<210> SEQ ID NO 48
<211> LENGTH: 20
<212> TYPE: PRT
<213> ORGANISM: Artificial Sequence
<220> FEATURE:
<223> OTHER INFORMATION: Modified region 43-62 of beta fibrin protein
<220> FEATURE:
<221> NAME/KEY: MISC_FEATURE
```

<222> LOCATION: (2)..(2)
<223> OTHER INFORMATION: X = Citrulline
<220> FEATURE:
<221> NAME/KEY: MISC_FEATURE
<222> LOCATION: (11)..(11)
<223> OTHER INFORMATION: X = Citrulline
<220> FEATURE:
<221> NAME/KEY: MISC_FEATURE
<222> LOCATION: (18)..(18)
<223> OTHER INFORMATION: X = Citrulline

<400> SEQUENCE: 48

Ala Xaa Gly His Arg Pro Leu Asp Lys Lys Xaa Glu Glu Ala Pro Ser
1               5                   10                  15

Leu Xaa Pro Ala
        20

<210> SEQ ID NO 49
<211> LENGTH: 20
<212> TYPE: PRT
<213> ORGANISM: Artificial Sequence
<220> FEATURE:
<223> OTHER INFORMATION: Modified region 43-62 of beta fibrin protein
<220> FEATURE:
<221> NAME/KEY: MISC_FEATURE
<222> LOCATION: (2)..(2)
<223> OTHER INFORMATION: X = Citrulline

<400> SEQUENCE: 49

Ala Xaa Gly His Arg Pro Leu Asp Lys Lys Arg Glu Glu Ala Pro Ser
1               5                   10                  15

Leu Arg Pro Ala
        20

<210> SEQ ID NO 50
<211> LENGTH: 20
<212> TYPE: PRT
<213> ORGANISM: Artificial Sequence
<220> FEATURE:
<223> OTHER INFORMATION: Modified region 43-62 of beta fibrin protein
<220> FEATURE:
<221> NAME/KEY: MISC_FEATURE
<222> LOCATION: (2)..(2)
<223> OTHER INFORMATION: X = Citrulline
<220> FEATURE:
<221> NAME/KEY: MISC_FEATURE
<222> LOCATION: (11)..(11)
<223> OTHER INFORMATION: X = Citrulline

<400> SEQUENCE: 50

Ala Xaa Gly His Arg Pro Leu Asp Lys Lys Xaa Glu Glu Ala Pro Ser
1               5                   10                  15

Leu Arg Pro Ala
        20

<210> SEQ ID NO 51
<211> LENGTH: 20
<212> TYPE: PRT
<213> ORGANISM: Artificial Sequence
<220> FEATURE:
<223> OTHER INFORMATION: Modified region 43-62 of beta fibrin protein
<220> FEATURE:
<221> NAME/KEY: MISC_FEATURE
<222> LOCATION: (2)..(2)
<223> OTHER INFORMATION: X = Citrulline
<220> FEATURE:
<221> NAME/KEY: MISC_FEATURE
<222> LOCATION: (18)..(18)
<223> OTHER INFORMATION: X = Citrulline -continued

```
<400> SEQUENCE: 51

Ala Xaa Gly His Arg Pro Leu Asp Lys Lys Arg Glu Glu Ala Pro Ser
1               5                   10                  15

Leu Xaa Pro Ala
            20

<210> SEQ ID NO 52
<211> LENGTH: 18
<212> TYPE: PRT
<213> ORGANISM: Homo sapiens
<220> FEATURE:
<221> NAME/KEY: PEPTIDE
<222> LOCATION: (1)..(18)
<223> OTHER INFORMATION: Region 72-89 of beta fibrin protein

<400> SEQUENCE: 52

Arg Ala Arg Pro Ala Lys Ala Ala Ala Thr Gln Lys Lys Val Glu Arg
1               5                   10                  15

Lys Ala

<210> SEQ ID NO 53
<211> LENGTH: 18
<212> TYPE: PRT
<213> ORGANISM: Artificial Sequence
<220> FEATURE:
<223> OTHER INFORMATION: Modified region 72-89 of beta fibrin protein
<220> FEATURE:
<221> NAME/KEY: MISC_FEATURE
<222> LOCATION: (16)..(16)
<223> OTHER INFORMATION: X = Citrulline

<400> SEQUENCE: 53

Arg Ala Arg Pro Ala Lys Ala Ala Ala Thr Gln Lys Lys Val Glu Xaa
1               5                   10                  15

Lys Ala

<210> SEQ ID NO 54
<211> LENGTH: 18
<212> TYPE: PRT
<213> ORGANISM: Artificial Sequence
<220> FEATURE:
<223> OTHER INFORMATION: Modified region 72-89 of beta fibrin protein
<220> FEATURE:
<221> NAME/KEY: MISC_FEATURE
<222> LOCATION: (3)..(3)
<223> OTHER INFORMATION: X = Citrulline

<400> SEQUENCE: 54

Arg Ala Xaa Pro Ala Lys Ala Ala Ala Thr Gln Lys Lys Val Glu Arg
1               5                   10                  15

Lys Ala

<210> SEQ ID NO 55
<211> LENGTH: 18
<212> TYPE: PRT
<213> ORGANISM: Artificial Sequence
<220> FEATURE:
<223> OTHER INFORMATION: Modified region 72-89 of beta fibrin protein
<220> FEATURE:
<221> NAME/KEY: MISC_FEATURE
<222> LOCATION: (3)..(3)
<223> OTHER INFORMATION: X = Citrulline
<220> FEATURE:
<221> NAME/KEY: MISC_FEATURE
<222> LOCATION: (16)..(16)
<223> OTHER INFORMATION: X = Citrulline
```

-continued

```
<400> SEQUENCE: 55

Arg Ala Xaa Pro Ala Lys Ala Ala Ala Thr Gln Lys Lys Val Glu Xaa
1               5                   10                  15

Lys Ala

<210> SEQ ID NO 56
<211> LENGTH: 18
<212> TYPE: PRT
<213> ORGANISM: Artificial Sequence
<220> FEATURE:
<223> OTHER INFORMATION: Modified region 72-89 of beta fibrin protein
<220> FEATURE:
<221> NAME/KEY: MISC_FEATURE
<222> LOCATION: (1)..(1)
<223> OTHER INFORMATION: X = Citrulline
<220> FEATURE:
<221> NAME/KEY: MISC_FEATURE
<222> LOCATION: (3)..(3)
<223> OTHER INFORMATION: X = Citrulline
<220> FEATURE:
<221> NAME/KEY: MISC_FEATURE
<222> LOCATION: (16)..(16)
<223> OTHER INFORMATION: X = Citrulline

<400> SEQUENCE: 56

Xaa Ala Xaa Pro Ala Lys Ala Ala Ala Thr Gln Lys Lys Val Glu Xaa
1               5                   10                  15

Lys Ala

<210> SEQ ID NO 57
<211> LENGTH: 18
<212> TYPE: PRT
<213> ORGANISM: Artificial Sequence
<220> FEATURE:
<223> OTHER INFORMATION: Modified region 72-89 of beta fibrin protein
<220> FEATURE:
<221> NAME/KEY: MISC_FEATURE
<222> LOCATION: (1)..(1)
<223> OTHER INFORMATION: X = Citrulline
<220> FEATURE:
<221> NAME/KEY: MISC_FEATURE
<222> LOCATION: (3)..(3)
<223> OTHER INFORMATION: X = Citrulline

<400> SEQUENCE: 57

Xaa Ala Xaa Pro Ala Lys Ala Ala Ala Thr Gln Lys Lys Val Glu Arg
1               5                   10                  15

Lys Ala

<210> SEQ ID NO 58
<211> LENGTH: 18
<212> TYPE: PRT
<213> ORGANISM: Artificial Sequence
<220> FEATURE:
<223> OTHER INFORMATION: Modified region 72-89 of beta fibrin protein
<220> FEATURE:
<221> NAME/KEY: MISC_FEATURE
<222> LOCATION: (1)..(1)
<223> OTHER INFORMATION: X = Citrulline
<220> FEATURE:
<221> NAME/KEY: MISC_FEATURE
<222> LOCATION: (16)..(16)
<223> OTHER INFORMATION: X = Citrulline

<400> SEQUENCE: 58

Xaa Ala Arg Pro Ala Lys Ala Ala Ala Thr Gln Lys Lys Val Glu Xaa
1               5                   10                  15

Lys Ala
```

```
<210> SEQ ID NO 59
<211> LENGTH: 18
<212> TYPE: PRT
<213> ORGANISM: Artificial Sequence
<220> FEATURE:
<223> OTHER INFORMATION: Modified region 72-89 of beta fibrin protein
<220> FEATURE:
<221> NAME/KEY: MISC_FEATURE
<222> LOCATION: (1)..(1)
<223> OTHER INFORMATION: X = Citrulline

<400> SEQUENCE: 59

Xaa Ala Arg Pro Ala Lys Ala Ala Ala Thr Gln Lys Lys Val Glu Arg
1               5                   10                  15

Lys Ala

<210> SEQ ID NO 60
<211> LENGTH: 18
<212> TYPE: PRT
<213> ORGANISM: Homo sapiens
<220> FEATURE:
<221> NAME/KEY: PEPTIDE
<222> LOCATION: (1)..(18)
<223> OTHER INFORMATION: Region 151-168 of beta fibrin

<400> SEQUENCE: 60

Leu Lys Asp Leu Trp Gln Lys Arg Gln Lys Gln Val Lys Asp Asn Glu
1               5                   10                  15

Asn Val

<210> SEQ ID NO 61
<211> LENGTH: 18
<212> TYPE: PRT
<213> ORGANISM: Artificial Sequence
<220> FEATURE:
<223> OTHER INFORMATION: Modified region 151-168 of beta fibrin protein
<220> FEATURE:
<221> NAME/KEY: MISC_FEATURE
<222> LOCATION: (8)..(8)
<223> OTHER INFORMATION: X = Citrulline

<400> SEQUENCE: 61

Leu Lys Asp Leu Trp Gln Lys Xaa Gln Lys Gln Val Lys Asp Asn Glu
1               5                   10                  15

Asn Val

<210> SEQ ID NO 62
<211> LENGTH: 19
<212> TYPE: PRT
<213> ORGANISM: Homo sapiens
<220> FEATURE:
<221> NAME/KEY: PEPTIDE
<222> LOCATION: (1)..(19)
<223> OTHER INFORMATION: Region 365-383 of beta fibrin

<400> SEQUENCE: 62

Ala Asn Lys Tyr Gln Ile Ser Val Asn Lys Tyr Arg Gly Thr Ala Gly
1               5                   10                  15

Asn Ala Leu

<210> SEQ ID NO 63
<211> LENGTH: 19
<212> TYPE: PRT
<213> ORGANISM: Artificial Sequence
<220> FEATURE:
```

-continued

<223> OTHER INFORMATION: Modified region 365-383 of beta fibrin protein
<220> FEATURE:
<221> NAME/KEY: MISC_FEATURE
<222> LOCATION: (12)..(12)
<223> OTHER INFORMATION: X = Citrulline

<400> SEQUENCE: 63

Ala Asn Lys Tyr Gln Ile Ser Val Asn Lys Tyr Xaa Gly Thr Ala Gly
1               5                   10                  15

Asn Ala Leu

<210> SEQ ID NO 64
<211> LENGTH: 26
<212> TYPE: PRT
<213> ORGANISM: Homo sapiens
<220> FEATURE:
<223> OTHER INFORMATION: Region 365-390 of beta fibrin protein
<220> FEATURE:
<221> NAME/KEY: PEPTIDE
<222> LOCATION: (1)..(26)
<223> OTHER INFORMATION: Region 365-390 of beta fibrin

<400> SEQUENCE: 64

Ala Asn Lys Tyr Gln Ile Ser Val Asn Lys Tyr Arg Gly Thr Ala Gly
1               5                   10                  15

Asn Ala Leu Met Asp Gly Ala Ser Gln Leu
            20                  25

<210> SEQ ID NO 65
<211> LENGTH: 26
<212> TYPE: PRT
<213> ORGANISM: Artificial Sequence
<220> FEATURE:
<223> OTHER INFORMATION: Modified region 365-383 of beta fibrin protein
<220> FEATURE:
<221> NAME/KEY: MISC_FEATURE
<222> LOCATION: (12)..(12)
<223> OTHER INFORMATION: X = Citrulline

<400> SEQUENCE: 65

Ala Asn Lys Tyr Gln Ile Ser Val Asn Lys Tyr Xaa Gly Thr Ala Gly
1               5                   10                  15

Asn Ala Leu Met Asp Gly Ala Ser Gln Leu
            20                  25

<210> SEQ ID NO 66
<211> LENGTH: 30
<212> TYPE: PRT
<213> ORGANISM: Homo sapiens
<220> FEATURE:
<223> OTHER INFORMATION: Modified region 365-383 of beta fibrin protein
<220> FEATURE:
<221> NAME/KEY: PEPTIDE
<222> LOCATION: (1)..(30)
<223> OTHER INFORMATION: Region 367-396 of beta fibrin

<400> SEQUENCE: 66

Lys Tyr Gln Ile Ser Val Asn Lys Tyr Arg Gly Thr Ala Gly Asn Ala
1               5                   10                  15

Leu Met Asp Gly Ala Ser Gln Leu Met Gly Glu Asn Arg Thr
            20                  25                  30

<210> SEQ ID NO 67
<211> LENGTH: 30
<212> TYPE: PRT
<213> ORGANISM: Artificial Sequence
<220> FEATURE:

```
<223> OTHER INFORMATION: Modified region 367-396 of beta fibrin protein
<220> FEATURE:
<221> NAME/KEY: MISC_FEATURE
<222> LOCATION: (29)..(29)
<223> OTHER INFORMATION: X = Citrulline

<400> SEQUENCE: 67

Lys Tyr Gln Ile Ser Val Asn Lys Tyr Arg Gly Thr Ala Gly Asn Ala
1               5                   10                  15

Leu Met Asp Gly Ala Ser Gln Leu Met Gly Glu Asn Xaa Thr
            20                  25                  30

<210> SEQ ID NO 68
<211> LENGTH: 30
<212> TYPE: PRT
<213> ORGANISM: Artificial Sequence
<220> FEATURE:
<223> OTHER INFORMATION: Modified region 367-396 of beta fibrin protein
<220> FEATURE:
<221> NAME/KEY: MISC_FEATURE
<222> LOCATION: (10)..(10)
<223> OTHER INFORMATION: X = Citrulline

<400> SEQUENCE: 68

Lys Tyr Gln Ile Ser Val Asn Lys Tyr Xaa Gly Thr Ala Gly Asn Ala
1               5                   10                  15

Leu Met Asp Gly Ala Ser Gln Leu Met Gly Glu Asn Arg Thr
            20                  25                  30

<210> SEQ ID NO 69
<211> LENGTH: 30
<212> TYPE: PRT
<213> ORGANISM: Artificial Sequence
<220> FEATURE:
<223> OTHER INFORMATION: Modified region 367-396 of beta fibrin protein
<220> FEATURE:
<221> NAME/KEY: MISC_FEATURE
<222> LOCATION: (10)..(10)
<223> OTHER INFORMATION: X = Citrulline
<220> FEATURE:
<221> NAME/KEY: MISC_FEATURE
<222> LOCATION: (29)..(29)
<223> OTHER INFORMATION: X = Citrulline

<400> SEQUENCE: 69

Lys Tyr Gln Ile Ser Val Asn Lys Tyr Xaa Gly Thr Ala Gly Asn Ala
1               5                   10                  15

Leu Met Asp Gly Ala Ser Gln Leu Met Gly Glu Asn Xaa Thr
            20                  25                  30

<210> SEQ ID NO 70
<211> LENGTH: 18
<212> TYPE: PRT
<213> ORGANISM: Homo sapiens
<220> FEATURE:
<223> OTHER INFORMATION: Region 373-390 of beta fibrin protein
<220> FEATURE:
<221> NAME/KEY: PEPTIDE
<222> LOCATION: (1)..(18)
<223> OTHER INFORMATION: Region 373-390 of beta fibrin

<400> SEQUENCE: 70

Asn Lys Tyr Arg Gly Thr Ala Gly Asn Ala Leu Met Asp Gly Ala Ser
1               5                   10                  15

Gln Leu

<210> SEQ ID NO 71
```

-continued

```
<211> LENGTH: 18
<212> TYPE: PRT
<213> ORGANISM: Artificial Sequence
<220> FEATURE:
<223> OTHER INFORMATION: Modified region 373-390 of beta fibrin protein
<220> FEATURE:
<221> NAME/KEY: MISC_FEATURE
<222> LOCATION: (4)..(4)
<223> OTHER INFORMATION: X = Citrulline

<400> SEQUENCE: 71

Asn Lys Tyr Xaa Gly Thr Ala Gly Asn Ala Leu Met Asp Gly Ala Ser
1               5                   10                  15

Gln Leu

<210> SEQ ID NO 72
<211> LENGTH: 18
<212> TYPE: PRT
<213> ORGANISM: Artificial Sequence
<220> FEATURE:
<223> OTHER INFORMATION: Modified region 365-383 of beta fibrin protein
<220> FEATURE:
<221> NAME/KEY: MISC_FEATURE
<222> LOCATION: (4)..(4)
<223> OTHER INFORMATION: X = Citrulline

<400> SEQUENCE: 72

Asn Lys Tyr Xaa Gly Thr Ala Gly Asn Ala Leu Met Asp Gly Ala Ser
1               5                   10                  15

Gln Leu

<210> SEQ ID NO 73
<211> LENGTH: 21
<212> TYPE: PRT
<213> ORGANISM: Artificial Sequence
<220> FEATURE:
<223> OTHER INFORMATION: Cycled peptide of beta fibrin
<220> FEATURE:
<221> NAME/KEY: MISC_FEATURE
<222> LOCATION: (5)..(5)
<223> OTHER INFORMATION: X = Citrulline
<220> FEATURE:
<221> NAME/KEY: MISC_FEATURE
<222> LOCATION: (18)..(18)
<223> OTHER INFORMATION: X = Citrulline
<220> FEATURE:
<221> NAME/KEY: cycled
<222> LOCATION: (1)..(21)
<223> OTHER INFORMATION: cycled peptide

<400> SEQUENCE: 73

Ala Arg Gly His Xaa Pro Leu Asp Lys Lys Arg Glu Glu Ala Pro Ser
1               5                   10                  15

Leu Xaa Pro Ala Asp
            20

<210> SEQ ID NO 74
<211> LENGTH: 24
<212> TYPE: PRT
<213> ORGANISM: Artificial Sequence
<220> FEATURE:
<223> OTHER INFORMATION: Cycled peptide of beta fibrin
<220> FEATURE:
<221> NAME/KEY: MISC_FEATURE
<222> LOCATION: (9)..(9)
<223> OTHER INFORMATION: X = Citrulline
<220> FEATURE:
<221> NAME/KEY: MISC_FEATURE
<222> LOCATION: (22)..(22)
<223> OTHER INFORMATION: X = Citrulline
```

```
<220> FEATURE:
<221> NAME/KEY: DISULFID
<222> LOCATION: (4)..(20)
<223> OTHER INFORMATION: Disulfide bridge between two cysteine amino
      acids

<400> SEQUENCE: 74

Gly Phe Phe Cys Ala Arg Gly His Xaa Pro Leu Asp Lys Lys Arg Glu
1               5                  10                  15

Glu Ala Pro Cys Leu Xaa Pro Ala
            20

<210> SEQ ID NO 75
<211> LENGTH: 15
<212> TYPE: PRT
<213> ORGANISM: Artificial Sequence
<220> FEATURE:
<223> OTHER INFORMATION: Cycled peptide of alfa fibrin
<220> FEATURE:
<221> NAME/KEY: MISC_FEATURE
<222> LOCATION: (14)..(14)
<223> OTHER INFORMATION: X = Citrulline
<220> FEATURE:
<221> NAME/KEY: DISULFID
<222> LOCATION: (2)..(10)
<223> OTHER INFORMATION: Disulfide bridge between two cysteine amino
      acids

<400> SEQUENCE: 75

His Cys Thr Lys Arg Gly His Ala Lys Cys Arg Pro Val Xaa Gly
1               5                  10                  15

<210> SEQ ID NO 76
<211> LENGTH: 15
<212> TYPE: PRT
<213> ORGANISM: Artificial Sequence
<220> FEATURE:
<223> OTHER INFORMATION: Cycled peptide of alfa fibrin
<220> FEATURE:
<221> NAME/KEY: MISC_FEATURE
<222> LOCATION: (11)..(11)
<223> OTHER INFORMATION: X = Citrulline
<220> FEATURE:
<221> NAME/KEY: MISC_FEATURE
<222> LOCATION: (14)..(14)
<223> OTHER INFORMATION: X = Citrulline
<220> FEATURE:
<221> NAME/KEY: DISULFID
<222> LOCATION: (2)..(10)
<223> OTHER INFORMATION: Disulfide bridge between two cysteine amino
      acids

<400> SEQUENCE: 76

His Cys Thr Lys Arg Gly His Ala Lys Cys Xaa Pro Val Xaa Gly
1               5                  10                  15

<210> SEQ ID NO 77
<211> LENGTH: 15
<212> TYPE: PRT
<213> ORGANISM: Artificial Sequence
<220> FEATURE:
<223> OTHER INFORMATION: Cycled peptide of alfa fibrin
<220> FEATURE:
<221> NAME/KEY: MISC_FEATURE
<222> LOCATION: (5)..(5)
<223> OTHER INFORMATION: X = Citrulline
<220> FEATURE:
<221> NAME/KEY: MISC_FEATURE
<222> LOCATION: (14)..(14)
<223> OTHER INFORMATION: X = Citrulline
<220> FEATURE:
<221> NAME/KEY: DISULFID
```

```
<222> LOCATION: (2)..(10)
<223> OTHER INFORMATION: Disulfide bridge between two cysteine amino
      acids

<400> SEQUENCE: 77

His Cys Thr Lys Xaa Gly His Ala Lys Cys Arg Pro Val Xaa Gly
1               5                   10                  15

<210> SEQ ID NO 78
<211> LENGTH: 21
<212> TYPE: PRT
<213> ORGANISM: Artificial Sequence
<220> FEATURE:
<223> OTHER INFORMATION: Cycled peptide of alfa fibrin
<220> FEATURE:
<221> NAME/KEY: MISC_FEATURE
<222> LOCATION: (14)..(14)
<223> OTHER INFORMATION: X = Citrulline
<220> FEATURE:
<221> NAME/KEY: DISULFID
<222> LOCATION: (2)..(19)
<223> OTHER INFORMATION: Disulfide bridge between two cysteine amino
      acids

<400> SEQUENCE: 78

His Cys Thr Lys Arg Gly His Ala Lys Ser Arg Pro Val Xaa Gly Ile
1               5                   10                  15

His Thr Cys Pro Leu
            20

<210> SEQ ID NO 79
<211> LENGTH: 21
<212> TYPE: PRT
<213> ORGANISM: Artificial Sequence
<220> FEATURE:
<223> OTHER INFORMATION: Cycled peptide of alfa fibrin
<220> FEATURE:
<221> NAME/KEY: MISC_FEATURE
<222> LOCATION: (11)..(11)
<223> OTHER INFORMATION: X = Citrulline
<220> FEATURE:
<221> NAME/KEY: MISC_FEATURE
<222> LOCATION: (14)..(14)
<223> OTHER INFORMATION: X = Citrulline
<220> FEATURE:
<221> NAME/KEY: DISULFID
<222> LOCATION: (2)..(19)
<223> OTHER INFORMATION: Disulfide bridge between two cysteine amino
      acids

<400> SEQUENCE: 79

His Cys Thr Lys Arg Gly His Ala Lys Ser Xaa Pro Val Xaa Gly Ile
1               5                   10                  15

His Thr Cys Pro Leu
            20

<210> SEQ ID NO 80
<211> LENGTH: 21
<212> TYPE: PRT
<213> ORGANISM: Artificial Sequence
<220> FEATURE:
<223> OTHER INFORMATION: Cycled peptide of alfa fibrin
<220> FEATURE:
<221> NAME/KEY: 5MISC_FEATURE
<222> LOCATION: (5)..(5)
<223> OTHER INFORMATION: X = Citrulline
<220> FEATURE:
<221> NAME/KEY: 5MISC_FEATURE
<222> LOCATION: (14)..(14)
<223> OTHER INFORMATION: X = Citrulline
<220> FEATURE:
```

```
<221> NAME/KEY: DISULFID
<222> LOCATION: (2)..(19)
<223> OTHER INFORMATION: Disulfide bridge between two cysteine amino
      acids

<400> SEQUENCE: 80

His Cys Thr Lys Xaa Gly His Ala Lys Ser Arg Pro Val Xaa Gly Ile
1               5                   10                  15

His Thr Cys Pro Leu
            20

<210> SEQ ID NO 81
<211> LENGTH: 38
<212> TYPE: PRT
<213> ORGANISM: Artificial Sequence
<220> FEATURE:
<223> OTHER INFORMATION: Chimeric polypeptide alfa fibrin/beta fibrin
<220> FEATURE:
<221> NAME/KEY: MISC_FEATURE
<222> LOCATION: (5)..(5)
<223> OTHER INFORMATION: X = Citrulline
<220> FEATURE:
<221> NAME/KEY: MISC_FEATURE
<222> LOCATION: (18)..(18)
<223> OTHER INFORMATION: X = Citrulline
<220> FEATURE:
<221> NAME/KEY: MISC_FEATURE
<222> LOCATION: (37)..(37)
<223> OTHER INFORMATION: X = Citrulline

<400> SEQUENCE: 81

Ala Arg Gly His Xaa Pro Leu Asp Lys Lys Arg Glu Glu Ala Pro Ser
1               5                   10                  15

Leu Xaa Pro Ala Gly Gly Gly His Ser Thr Lys Arg Gly His Ala Lys
            20                  25                  30

Ser Arg Pro Val Xaa Gly
            35

<210> SEQ ID NO 82
<211> LENGTH: 38
<212> TYPE: PRT
<213> ORGANISM: Artificial Sequence
<220> FEATURE:
<223> OTHER INFORMATION: Chimeric polypeptide alfa fibrin/beta fibrin
<220> FEATURE:
<221> NAME/KEY: MISC_FEATURE
<222> LOCATION: (5)..(5)
<223> OTHER INFORMATION: X = Citrulline
<220> FEATURE:
<221> NAME/KEY: MISC_FEATURE
<222> LOCATION: (18)..(18)
<223> OTHER INFORMATION: X = Citrulline
<220> FEATURE:
<221> NAME/KEY: MISC_FEATURE
<222> LOCATION: (34)..(34)
<223> OTHER INFORMATION: X = Citrulline
<220> FEATURE:
<221> NAME/KEY: MISC_FEATURE
<222> LOCATION: (37)..(37)
<223> OTHER INFORMATION: X = Citrulline

<400> SEQUENCE: 82

Ala Arg Gly His Xaa Pro Leu Asp Lys Lys Arg Glu Glu Ala Pro Ser
1               5                   10                  15

Leu Xaa Pro Ala Gly Gly Gly His Ser Thr Lys Arg Gly His Ala Lys
            20                  25                  30

Ser Xaa Pro Val Xaa Gly
            35
```

```
<210> SEQ ID NO 83
<211> LENGTH: 38
<212> TYPE: PRT
<213> ORGANISM: Artificial Sequence
<220> FEATURE:
<223> OTHER INFORMATION: Chimeric polypeptide alfa fibrin/beta fibrin
<220> FEATURE:
<221> NAME/KEY: MISC_FEATURE
<222> LOCATION: (5)..(5)
<223> OTHER INFORMATION: X = Citrulline
<220> FEATURE:
<221> NAME/KEY: MISC_FEATURE
<222> LOCATION: (18)..(18)
<223> OTHER INFORMATION: X = Citrulline
<220> FEATURE:
<221> NAME/KEY: MISC_FEATURE
<222> LOCATION: (28)..(28)
<223> OTHER INFORMATION: X = Citrulline
<220> FEATURE:
<221> NAME/KEY: MISC_FEATURE
<222> LOCATION: (37)..(37)
<223> OTHER INFORMATION: X = Citrulline

<400> SEQUENCE: 83

Ala Arg Gly His Xaa Pro Leu Asp Lys Lys Arg Glu Glu Ala Pro Ser
1               5                   10                  15

Leu Xaa Pro Ala Gly Gly Gly His Ser Thr Lys Xaa Gly His Ala Lys
            20                  25                  30

Ser Arg Pro Val Xaa Gly
            35
```